United States Patent
Kwon et al.

(10) Patent No.: US 11,395,836 B2
(45) Date of Patent: *Jul. 26, 2022

(54) CANCER ANTIGEN SPECIFIC CYTOTOXIC T CELL

(71) Applicant: Eutilex Co., Ltd., Seoul (KR)

(72) Inventors: Byoung S. Kwon, Seoul (KR); Young Ho Kim, Seoul (KR); Mun Ki Kim, Seoul (KR); Kwang Hee Kim, Seoul (KR); You Hyun Kang, Seoul (KR)

(73) Assignee: Eutilex Co., Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/715,695

(22) Filed: Dec. 16, 2019

(65) Prior Publication Data

US 2020/0188437 A1 Jun. 18, 2020

Related U.S. Application Data

(63) Continuation of application No. PCT/KR2019/010240, filed on Aug. 12, 2019.

(60) Provisional application No. 62/717,236, filed on Aug. 10, 2018.

(51) Int. Cl.
*A61K 35/17* (2015.01)
*A61P 35/00* (2006.01)
*C07K 14/705* (2006.01)
*C12N 5/0783* (2010.01)

(52) U.S. Cl.
CPC .............. *A61K 35/17* (2013.01); *A61P 35/00* (2018.01); *C07K 14/70503* (2013.01); *C12N 5/0636* (2013.01)

(58) Field of Classification Search
CPC ............ A61K 35/17; A61K 39/001186; A61K 39/001188; A61K 39/001157; A61K 39/001153; A61K 39/12; C12N 5/0636; C12N 5/0638; C12N 2501/2302; C12N 2501/2307; C12N 2501/2315; C12N 2501/2321
See application file for complete search history.

(56) References Cited

U.S. PATENT DOCUMENTS

2004/0209363 A1* 10/2004 Watts .................... C12N 5/0636
435/456
2004/0228848 A1* 11/2004 Har-Noy .............. C12N 5/0636
424/93.71

FOREIGN PATENT DOCUMENTS

| KR | 100882445 | 2/2008 | |
|----|-----------|--------|---|
| KR | 101103603 | 1/2012 | |
| KR | 101503341 | 3/2015 | |
| WO | WO-2018005712 A1 * | 1/2018 | .............. A61P 37/04 |

OTHER PUBLICATIONS

Cheever et al, Clinical Cancer Research, 2009, vol. 15, pp. 5323-5337 (Year: 2009).*
Gottschalk et al (Leukemia & Lymphoma, 2005, vol. 46, pp. 1-10) (Year: 2005).*
(Hochst and Diehl, Oncoimmunology, 2012, vol. 1, pp. 1620-1622) (Year: 2012).*
Li et al (Journal of Experimental and Clinical Cancer Research, 2009, vol. 28, 8 pages) (Year: 2009).*
Abstract of Lu et al (Chinese Medical Journal, 2007, vol. 120, pp. 1042-1046) (Year: 2007).*
Cui et al (Disease Markers, 2013, vol. 35, pp. 915-923) (Year: 2013).*
Simpson et al (Nature Reviews Cancer, 2005, vol. 5, pp. 615-625) (Year: 2005).*
Miyagawa et al (Oncology, 2006, vol. 70, pp. 54-2) (Year: 2006).*
Zhang et al (European Journal of Immunology, 2005, vol. 35, pp. 1066-1075) (Year: 2005).*
Zhang et al (Journal of immunology, 2005, vol. 174, pp. 2404-2411) (Year: 2005).*
Atanackovic et al (2004, vol. 172, pp. 3289-3296) (Year: 2004).*
Oka et al (Oncology Research and Treatment, 2017, vol. 40, pp. 682-690) (Year: 2017).*
Oqawa et al (Blood, 2003, vol. 101, pp. 1698-1704) (Year: 2003).*
Cilloni et al (Journal of Clinical Oncology, 2009, vol. 27, pp. 5195-5201) (Year: 2009).*
Eom et al (Journal of Immunotherapy, 2016, vol. 39, pp. 140-148) (Year: 2016).*
Choi et al (Journal of Immunotherapy, 2014, vol. 37, pp. 225-236) (Year: 2014).*
Pollack et al (Journal of Immunotherapy, 2014, vol. 2, 10 pages) (Year: 2014).*
Watanabe et al (International Journal of Hematology, 2008, vol. 88, pp. 311-320) (Year: 2008).*
Pollack et al (Journal of Immunotherapy, 2014, vol. 2, supplemental) (Year: 2014).*
Wang et al (International Journal of Cancer, 2014, vol. 136, pp. 1751-1768) (Year: 2014).*
Wang et al (Oncoimmunology, 2016, vol. 5, e107267, 11 pages) (Year: 2016).*
Zhang et al (Asian Pacific Journal of Cancer Prevention, 2015, vol. 16, pp. 1487-1494) (Year: 2015).*
Calcedo et al (PNAS, 2017, vol. 114, pp. 1655-1659) (Year: 2017).*
Call et al, "Isolation and characterization of a zinc finger polypeptide gene at the human chromosome 11 Wilms'tumor locus," Cell, 1990, 60:3:509-520.
Decoster et al, Vaccination therapy for non-small-cell lung cancer: review of agents in phase III development, Annals of Oncoloqv, 2012, 23:5:1387-1393.

(Continued)

*Primary Examiner* — Karen A. Canella
(74) *Attorney, Agent, or Firm* — Oblon, McClelland, Maier & Neustadt, L.L.P.

(57) ABSTRACT

The present invention relates to a pharmaceutical composition for preventing or treating cancer comprising cancer antigen-specific cytotoxic T cells; the pharmaceutical composition comprises about 7×10⁶ cells/mL or more, and of the about 7×10⁶ cells/mL, about 90% or more are CD8+ T cells.

14 Claims, 11 Drawing Sheets

Specification includes a Sequence Listing.

(56) References Cited

OTHER PUBLICATIONS

Gnjatic et al, "NY-ESO-1: review of an immunogenic tumor antigen," Adv. Cancer Res., 2006, 95:1-30.
Kim et al., "Specific association of human telomerase activity with immortal cells and cancer", Science, 266: 2011-2015, 1994.
Nakahara et al, "Expression of the Wilms' tumor gene product WT1 in glioblastomas and medulloblastomas," Brain Tumor Pathology, 2004, 21:113-116.
GenBank Accession No. AA061088.1, "Stratagene mouse testis (#937308) Mus musculus cDNA clone Image: 514818 5–,mRNA sequence," Sep. 23, 1996, 1 page.

* cited by examiner

[TRANSLATION]

A. Conventional production process

| Epitope screening | Selection of 3-4 peptide species for production | Initial proliferation of antigen-specific CD8 T cells (using IL-2) | Antigen re-stimulation (inducing 4-1BB expression) | Selective isolation of antigen-specific CD8 T cells (using Anti-4-1-BB coated plate) | Mass production of antigen-specific CD8 T cells |
|---|---|---|---|---|---|
| 15 days | | 14 days | 1 day | 2 days | 14 days |

B. New production process

| Epitope screening | Selection of 3-4 peptide species for production | Initial proliferation of antigen-specific CD8 T cells (using IL-2) | Selective isolation of antigen-specific CD8 T cells (using automatic cell counter) | Mass production of antigen-specific CD8 T cells |
|---|---|---|---|---|
| 7 days | | 9 days | 0 days | 11 days |

C. New production process

| Epitope screening | Selection of 3-4 peptide species for production | Initial proliferation of antigen-specific CD8 T cells (using IL-2 + IL-7) (using IL-2 + IL-15) (using IL-2 + IL-21) | Selective isolation of antigen-specific CD8 T cells (using automatic cell counter) | Mass production of antigen-specific CD8 T cells |
|---|---|---|---|---|
| 7 days | | 7 days | 0 days | 11 days |

FIG. 1

D. New production process

| Epitope screening | Selection of 3-4 peptide species for production | Initial proliferation of antigen-specific CD8 T cells (using IL-2) | Antigen re-stimulation (inducing 4-1BB expression) | Selective isolation of antigen-specific CD8 T cells (using automatic cell counter) | Mass production of antigen-specific CD8 T cells |
|---|---|---|---|---|---|
| 15 days | | 14 days | 1 day | 0 days | 11 days |

E. New production process

| Epitope screening | Selection of 3-4 peptide species for production | Initial proliferation of antigen-specific CD8 T cells (using IL-2) | Antigen re-stimulation (inducing 4-1BB expression) | Selective isolation of antigen-specific CD8 T cells (using Anti-4-1-BB coated plate) | Mass production of antigen-specific CD8 T cells |
|---|---|---|---|---|---|
| 15 days | | 14 days | 1 day | 0 days | 14 days |

(translation cont'd)

FIG. 1

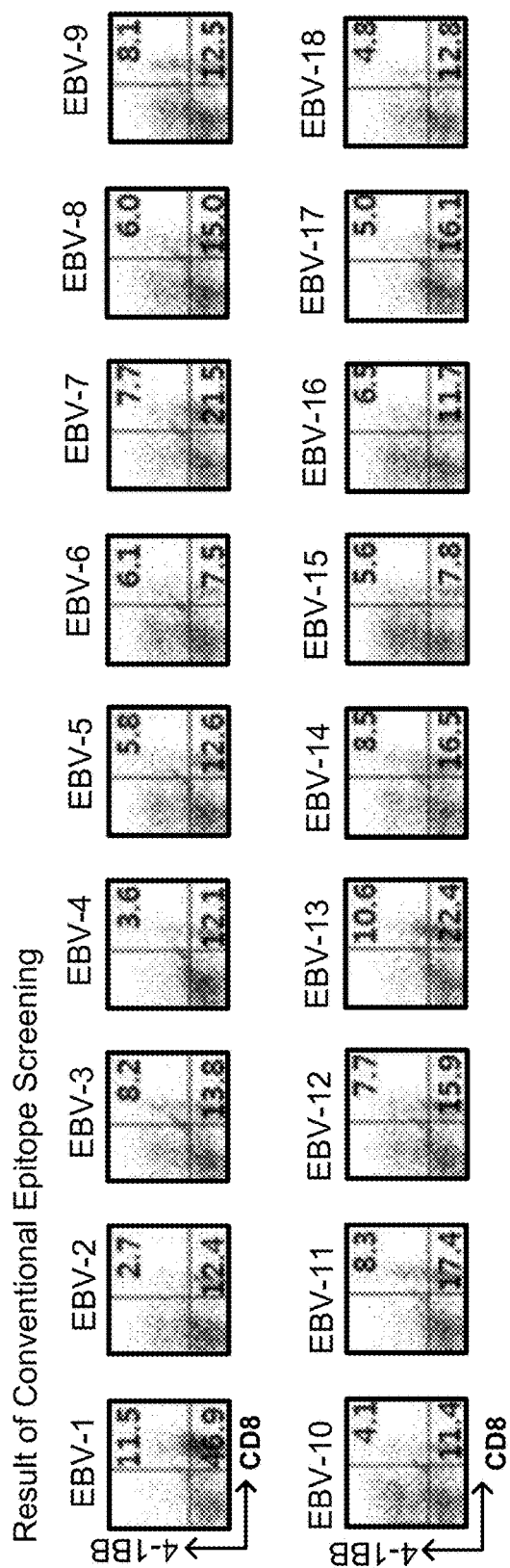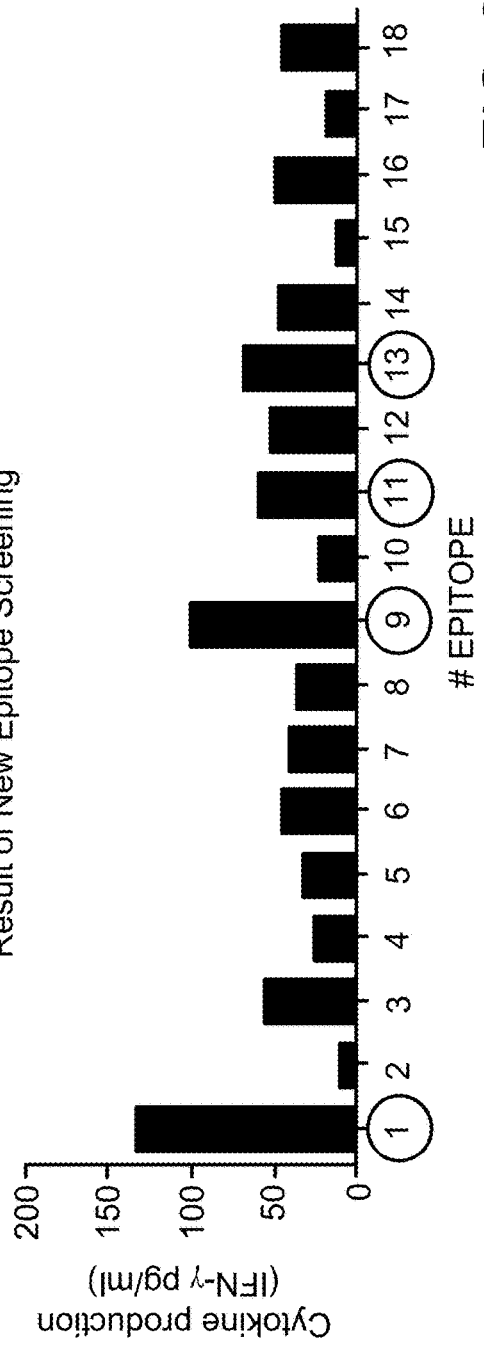

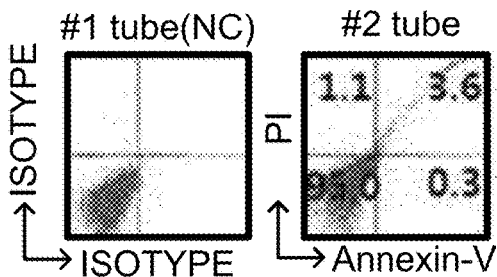
FIG. 4A
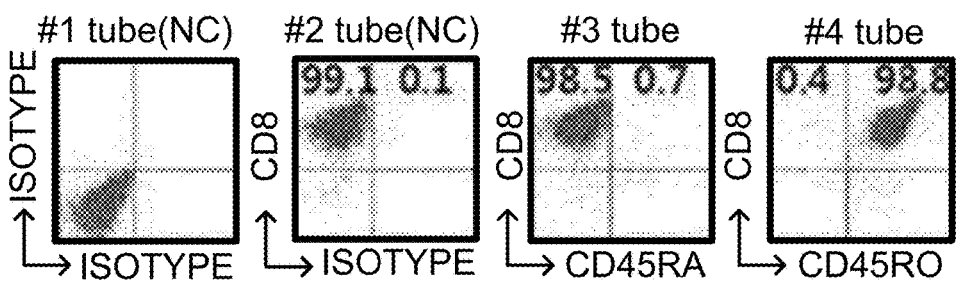
FIG. 4B
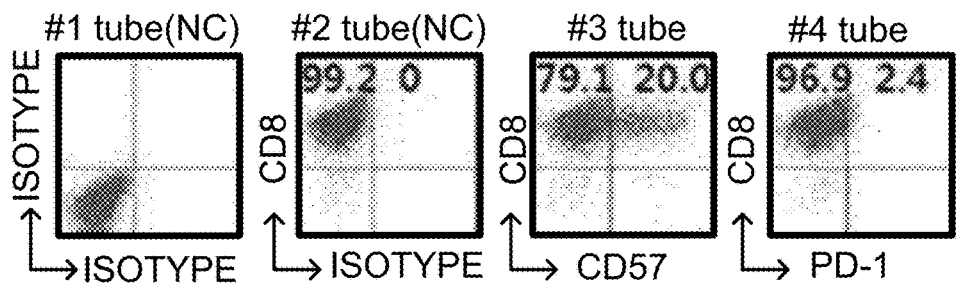
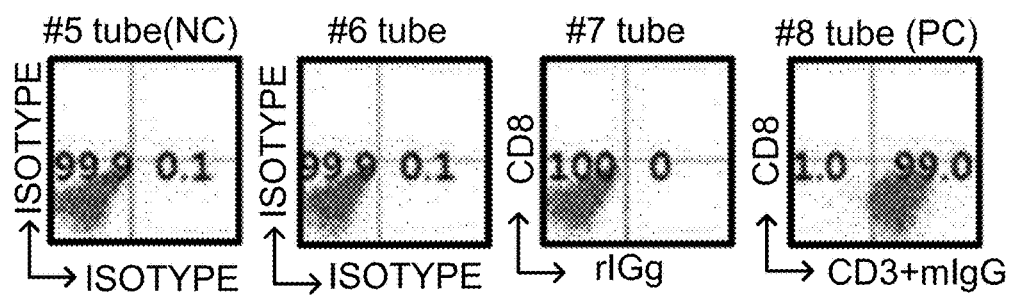
FIG. 4C

US 11,395,836 B2

CANCER ANTIGEN SPECIFIC CYTOTOXIC T CELL

CROSS-REFERENCE TO RELATED APPLICATIONS

This application is a continuation application claiming priority to PCT Application No. PCT/KR2019/010240, filed on Aug. 12, 2019, which claims priority to and the benefit of U.S. Patent Application No. 62/717,236, filed on Aug. 10, 2018. The entire contents of the foregoing are, the disclosure of which are incorporated herein incorporated by reference in their entirety.

STATEMENT REGARDING SEQUENCE LISTING

The Sequence Listing associated with this application is provided in text form in lieu of a paper copy, and is hereby incorporated by reference into the specification. The name of the text file containing the Sequence Listing is sequencelisting.txt. The text file is 22.6 KB, and was created and submitted electronically via EFS-Web on Jun. 23, 2020.

TECHNICAL FIELD

The present invention relates to a cancer antigen-specific cytotoxic T cell, and to a pharmaceutical composition comprising the same.

BACKGROUND ART

Because CD8+ T cells have a comparatively simple function compared to other cells such as dendritic cells, CD4+ T and NK cells, unexpected side effects in anti-cancer immunotherapy are less likely to occur. In general, MHC class I/peptide multimers are used to isolate antigen-specific CD8+ T cells, but this method has the drawback that because the rate of cell death due to apoptosis after cell isolation is high, long-term incubation is necessary in order to produce a sufficient quantity of antigen-specific CD8+ T cells. Therefore, a surrogate marker capable of isolating antigen-specific CD8+ T cells by replacing the MEW multimers that stimulate T cell receptors (TCR) is required; for this purpose, the protein 4-1BB (CD137) is used.

4-1BB is an inducible co-stimulatory molecule and is expressed in activated T cells; in particular, stimulation via 4-1BB is known not only to enhance the activity of CD8+ T cells, but also to act to inhibit activation-induced cell death (AICD) by increasing the expression of anti-apoptotic molecules such as Bcl-2, Bcl-XL, and Bfl-1.

The present inventors have previously disclosed methods of isolating and proliferating antigen-specific CD8+ T cells using the expression of 4-1BB by activated CD8+ T cells, or using an anti-4-1BB antibody or pentameric COMP-4-1BBL protein (Republic of Korea Registered Patents 100882445, 101103603, 101503341). The background art for the present specification is the T cell or method of manufacturing the same that the above patents disclose.

These patent references disclose techniques for isolating and mass-culturing antigen-specific CD8+ T cells for foreign antigens in the form of virus antigens (EBV/LMP2A, CMV/pp65) or autologous antigens (WT1, hTERT, NY-ESO-1, and the like). However, in the existing technique for isolating antigen-specific CD8+ T cells using a plate coated with anti-4-1BB antibody coated plate, the purity of the isolated cells varies greatly with the skill of the operator, and the process of culturing the cells is also very complex. Moreover, because the production process takes 30 days or more, there is currently a continuing need to shorten as much as possible the time needed to produce cell therapeutics for clinical applications.

Accordingly, it is necessary to isolate antigen-specific CD8+ T cells more easily and to shorten the overall incubation process by mass proliferating these cells quickly.

DETAILED DESCRIPTION OF THE INVENTION

Technical Task

The present invention aims to provide a CD8+ T cell-containing pharmaceutical composition prepared at a high degree of purity.

In addition, the present invention aims to provide an epitope advance screening method for screening epitopes derived from cancer antigens that are required for producing cancer antigen-specific CD8+ T cells within 7 days, and a method for selectively isolating and mass-proliferating antigen-specific CD8+ T cells within 20 days.

Means of Solving the Problem

1. A pharmaceutical composition for preventing or treating cancer comprising cancer antigen-specific cytotoxic T cells, wherein the pharmaceutical composition comprises at least about $7\times10^6$ cells/mL, and of this about $7\times10^6$ cells/mL, at least about 90% is CD8+ T cells, and either at least 80% of these CD8+ T cells are CD45RO-expressing cells, or 20% or less of these CD8+ T cells are CD45RA-expressing cells.

2. A pharmaceutical composition for preventing or treating cancer according to Item 1, wherein the pharmaceutical composition is manufactured by a method comprising: (a) a step of selecting a cancer antigen-derived epitope present in the cancer patient's blood; (b) incubating a peripheral blood mononuclear cell (PBMC) isolated from the blood of a cancer patient with the epitope and at least one cytokine selected from the group consisting of IL-2, IL-7, IL-15 and IL-21; (c) selecting cells expressing both CD8 and 4-1BB from among the cells cultured in step (b); and (d) incubating the T cells selected in step (c) with anti-CD3 antibody and IL-2.

3. A pharmaceutical composition for preventing or treating cancer according to Item 1, wherein the cancer antigen is at least one selected from the group made up of hTERT, NY-ESO1, MAGE-A3, WT1 and EBV.

4. A pharmaceutical composition for preventing or treating cancer according to Item 2, wherein at least 2 species of epitopes are used at step (a) or (b).

5. A pharmaceutical composition for preventing or treating cancer according to Item 2, wherein step (c) is performed using a closed-system flow cytometer.

6. A method of manufacturing a pharmaceutical composition for preventing or treating cancer, comprising: (a) a step of selecting a cancer antigen-derived epitope present in the cancer patient's blood; (b) a step of incubating a peripheral blood mononuclear cell (PBMC) isolated from the blood of a cancer patient with the epitope and at least one cytokine selected from the group consisting of IL-2, IL-7, IL-15 and IL-21; (c) a step of selecting cells expressing both CD8 and 4-1BB from among the cells cultured in step (b); and (d) a step of incubating the T cells selected in step (c) with anti-CD3 antibody and IL-2; and wherein the pharmaceutical composition comprises at least about $7\times10^6$ cells/ mL of cancer antigen-specific cytotoxic T cells, and wherein of this about 7×10⁶ cells/mL, at least about 90% is CD8+ T cells, and either at least 80% of these CD8+ T cells are CD45RO-expressing cells, or 20% or less of these CD8+ T cells are CD45RA-expressing cells.

7. A method according to Item 6, wherein the cancer antigen is at least one selected from the group made up of hTERT, NY-ESO1, MAGE-A3, WT1 and EBV.

8. A method according to Item 6, wherein at least 2 species of epitopes are used at step (a) or (b).

9. A method according to Item 6, wherein step (c) is performed using a closed-system flow cytometer.

10. A method of manufacturing a pharmaceutical composition for preventing or treating cancer, comprising a step of administering a pharmaceutical composition for preventing or treating cancer that comprises a pharmaceutically effective quantity of cancer antigen-specific cytotoxic T cells; wherein the pharmaceutical composition comprises at least about 7×10⁶ cells/mL of cancer antigen-specific cytotoxic T cells, and wherein of this about 7×10⁶ cells/mL, at least about 90% is CD8+ T cells, and either at least 80% of these CD8+ T cells are CD45RO-expressing cells, or 20% or less of these CD8+ T cells are CD45RA-expressing cells.

11. A method according to Item 10, wherein the pharmaceutical composition is manufactured by a method comprising: (a) a step of selecting a cancer antigen-derived epitope present in the cancer patient's blood; (b) incubating a peripheral blood mononuclear cell (PBMC) isolated from the blood of a cancer patient with the epitope and at least one cytokine selected from the group consisting of IL-2, IL-7, IL-15 and IL-21; (c) selecting cells expressing both CD8 and 4-1BB from among the cells cultured in step (b); and (d) incubating the T cells selected in step (c) with anti-CD3 antibody and IL-2.

12. A method according to Item 10, wherein the cancer antigen is at least one selected from the group made up of hTERT, NY-ESO1, MAGE-A3, WT1 and EBV.

13. A method according to Item 11, wherein at least 2 species of epitopes are used at step (a) or (b).

14. A method according to Item 11, wherein step (c) is performed using a closed-system flow cytometer.

Effect of the Invention

The CD8+ T cell-containing pharmaceutical composition of the present invention may comprise cancer antigen-specific CD8+ T cells at a high degree of purity.

The CD8+ T cell-containing pharmaceutical composition of the present invention has superior efficacy against cancer.

The CD8+ T cell-containing pharmaceutical composition of the present invention has superior clinical effectiveness as a T cell therapeutic.

The CD8+ T cell production method of the present invention is able to screen the epitopes derived from cancer antigens that are required for the production of cancer antigen-specific CD8+ T cells rapidly and straightforwardly.

The CD8+ T cell production method of the present invention makes it possible to selectively isolate and mass-culture cancer antigen-specific CD8+ T cells with high purity.

The CD8+ T cell production method of the present invention makes it possible to rapidly produce cancer antigen-specific CD8+ T cells.

The CD8+ T cell production method of the present invention may be applied to the GMP process.

The CD8+ T cell production method of the present invention makes it possible to selectively isolate and mass-culture cancer antigen-specific CD8+ T cells with high purity.

BRIEF DESCRIPTION OF THE DRAWINGS

FIG. 1A schematically depicts a conventional process for producing cancer antigen-specific CD8+ T cells. FIGS. 1B, 1C, 1D, and 1E schematically depict new processes for producing cancer antigen-specific CD8+ T cells.

FIG. 2A shows epitope screening results according to a conventional method. FIG. 2B shows epitope screening results according to the method of the present invention.

FIGS. 4A-4E show the results of testing against the self-assessment criteria and the test items for the T cell therapeutic product.

BEST MODE OF CARRYING OUT THE INVENTION

Figure 3:
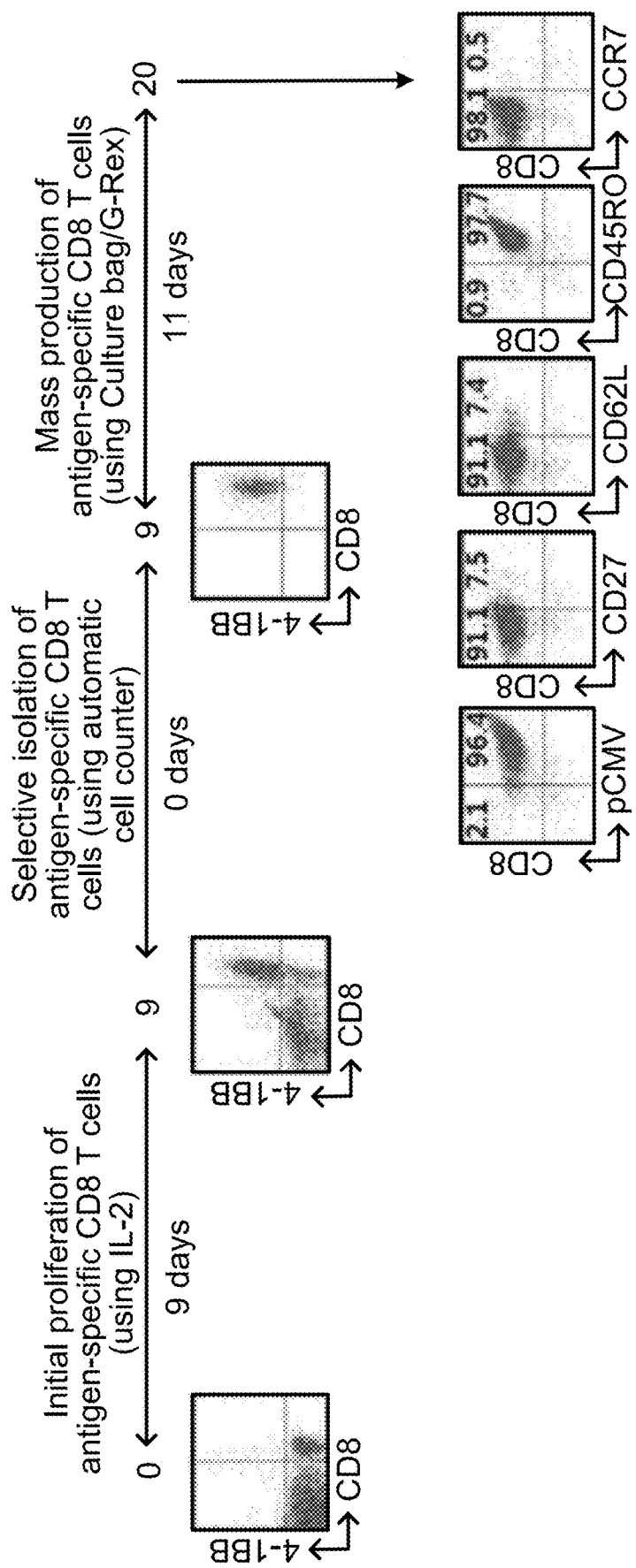
FIG. 3 shows the results of confirmation of the phenotype of the antigen-specific CD8+ T cells produced by the antigen-specific CD8+ T cell therapeutic production process and the 20-day process.

The present invention relates to a pharmaceutical composition for preventing or treating cancer comprising cytotoxic T cells specific for cancer antigens (for example, EBV, CMV, hTERT, NY-ESO-1, WT1, MAGE-A3, etc.) at a high degree of purity.

In addition, in the field of cancer cell therapy using cancer cell-specific immune cells, the present invention relates to a method of isolating and proliferating cancer antigen-specific cytotoxic T cells that makes it possible to rapidly screen the cancer peptides (epitopes) necessary for the production of cancer antigen-specific cytotoxic T cells within 7 days; and to use them to quickly and simply isolate and mass-culture antigen-specific CD8+ T cells at high purity within 20 days.

The pharmaceutical composition of the present invention comprises cytotoxic T cells specific for cancer antigens (for example, EBV, CMV, hTERT, NY-ESO-1, WT1, MAGE-A3, Neo-Antigen, etc.); the time taken from primary proliferation to freezing after completion of the final T cell mass culture may be 31 days; improved production processes may also take 26 days, 20 days or 15 days. (FIG. 1)

The pharmaceutical composition of the present invention may comprise 65% or more cancer antigen-specific cytotoxic T cells (for example, CD8+ T cells). For example, the pharmaceutical composition of the present invention may comprise 65%, 70%, 75%, 80%, 85%, 90%, 95%, or 99% or more CD8+ T cells.

In one embodiment of the present invention, the pharmaceutical composition of the present invention may be one or more species of TCRptype expressed in 10% or more, or 20% or more of the CD8+ T cells.

In one embodiment of the present invention, cells expressing CD45RO make up at least 60%, at least 70%, at least 80%, at least 90%, or at least 95% of the CD8+ T cells of the pharmaceutical composition of the present invention; in another embodiment of the present invention, at least 80% of the CD8+ T cells of the pharmaceutical composition of the present invention are cells expressing CD45RO.

In one embodiment of the present invention, cells expressing CD45RA are 30% or less, 20% or less, 10% or less, or 5% or less, of the CD8+ T cells of the pharmaceutical composition of the present invention; in another embodiment of the present invention, 20% of the CD8+ T cells of the pharmaceutical composition of the present invention are cells expressing CD45RA.

The pharmaceutical composition of the present invention may be prepared by the manufacturing method below.

One aspect of the present application relates to a method of proliferating and isolating cancer antigen-specific CD8+ T cells; one embodiment of this method comprises a) a step of first culturing a PBMC (peripheral blood mononuclear cell) isolated from the blood of a cancer patient with a respective peptide derived from a cancer antigen, and screening activated T cells to screen for cancer antigen CD8+ T cell epitopes; b) a step of culturing the PBMCs isolated from the blood of cancer patients in a medium comprising the screened epitope and at least one cytokine selected from the group made up of IL-2, IL-7, IL-15 and IL-21, thereby inducing 4-1BB expression in the PBMC; and c) a step of staining the cells in which 4-1BB expression was induced with anti-4-1BB antibody and anti-CD8 antibody and then isolating them.

The method of the present invention for screening antigen epitopes for the production of antigen-specific CD8+ T cells, and isolating and proliferating antigen-specific CD8+ T cells, will be described step by step below.

In the method according to the present application, the step of CD8+ cell epitope sorting or screening is intended to increase the avidity for cancer cells or alternatively to increase the concentration of cancer antigen-specific CD8+ T cells that are present in blood at a low concentration of 0.1% or below, and is the first step that enables selectively proliferating and isolating cancer antigen-specific CD8+ T cells.

In this step, epitopes from various cancer antigens (for example EBV, CMV, hTERT, NY-ESO-1, WT1, MAGE-A3, etc.) that CD8+ cells are able to recognize may be used. However, this depends on the individual patient's condition.

In other words, even if the same type of cancer antigen in cancer antigens such as for example EBV, CMV, hTERT, NY-ESO-1, WT1, MAGE-A3, etc., the part that may act as epitope depends on each patient's HLA-A type and condition. Therefore, even within the same cancer antigen, it is important to select and use the cancer antigen CD8+ T cell epitopes present in the blood of individual cancer patients through epitope screening, because the peptide portions that may act as antigen epitopes are different for each cancer patient. Generally, for use in preparing T cell therapeutics, 3-4 types of peptides are selected that act as epitopes.

The method according to the present application comprises selecting epitopes that are optimal for selecting and proliferating CD8+ T cells in individuals, from a variety of cancer antigens; various cancer antigens that achieve this objective may be used, including both autologous and non-autologous antigens.

For example, autologous cancer antigens derived from the patient's own genes include hTERT (GenBank: BAC11010.1; SEQ ID NO: 1), WT1 (GenBank: AA061088.1; SEQ ID NO: 2), NY-ESO1 (GenBank: CAA05908.1; SEQ ID NO: 3), MAGE-A3 (NCBI Reference Sequence: NP 005353.1; SEQ ID NO: 4) and cancer-specific mutant antigens such as neoantigens, mutated P53, RAS, and the like may include tumor suppressor or trigger genes, and foreign cancer antigens such as carcinogenic virus antigens such as CMV, EBV, HPV and the like.

However, the characteristics of the invention disclosed in the present application, which selects an optimal epitope for each individual from various cancer antigens specific for each type of cancer and uses these to produce T cells, are not limited hereto. Known autologous cancer antigens are for example WT1, hTERT, NY-ESO1, Mesothelin, MAGE's, and the like. For example, hTERT, a self-type cancer antigen, is an enzyme that synthesizes telomeric DNA at the termini of chromosomes, which cancer cells excessively active to evade telomere-dependent cell death, and which is known as a target antigen for various solid cancers including lung, stomach and pancreatic cancer (Kim N W, et al. Science. 1994; 266: 2011-2015); WT1 is a gene associated with Wilms tumor and encodes a zinc finger transcription factor, a protein that is involved in cell proliferation, differentiation, apoptosis, and organ development, and is known as a target antigen for cerebrospinal cancer, lung cancer and the like (Call K M, et al., Cell. 1990. 60: 509-520; Nakahara Y, et al., Brain Tumor Pathol. 2004. 21: 113-6). In addition, the aforementioned NY-ESO1 is a cancer testis antigen (CTA) protein, and is known to be expressed chiefly in germ cells, sarcoma, and various cancer cells including breast cancer (Gnjatic S, et al., Adv Cancer Res. 2006; 95:1-30). MAGE-A3 is a protein belonging to the melanoma-associated antigen family, and it is unknown what function it performs in healthy cells, but it is known to overexpress various cancer cells including lung cancer, sarcoma and melanoma, and has been evaluated as a suitable target antigen for cancer immunotherapy (Decoster L, et al., Ann Oncol. 2012 June; 23 (6): 1387-93). Accordingly, in the method of the present application, cancer antigens known to be associated with particular cancers may be used for producing individual cancer antigen CD8+ T cells.

In addition, viral cancer antigens are known, including for example EBV, HPV, MC polyoma virus, HBV, HCV, and CMV; Epstein-Barr virus antigen is known as a target antigen for Hodgkin's lymphoma, nasopharyngeal carcinoma, stomach cancer, Burkitt's lymphoma, and NK/T lymphoma, and human papilloma virus antigens are known as target antigens of uterine cancer and head and neck cancer, while MC polyoma virus is known as the target antigen of Merkel cell cancer. Hepatitis B and C viruses are also known as target cells of liver cancer.

As tissue-specific cancer antigens, tyrosinase, GP100, and MNRT-1 are known as melanoma target antigens, and PSMA, PAP, and PSA are known as prostate cancer target antigens.

Two, three, four, five or more peptides are used that are derived from cancer antigens. In particular, considering that 3-4 types of peptides acting as epitopes are generally used for the preparation of T cell therapeutics, the peptides derived from cancer antigens used number at least 4 or more, 5 or more, 6 or more, 7 or more, 8 or more, 9 or more, or more, but are not limited hereto, and may be left to the determination of the skilled person in view of the features of the method of the present application and the art of the relevant field.

The epitope screening step that the method of the present application comprises differs from the conventional epitope screening process in that during screening, epitopes may be selected by a method of screening activated T cells (for example, 4-1BB+CD8+ T cells). For example, after antigen stimulation, activated T cells are selected, and antigen epitopes that are able to induce such cells may be selected by detecting the presence and amount of activated T cells (for example, 4-1BB+CD8+ T cells) that are present. The activated T cells (for example, 4-1BB+CD8+ T cells) may be screened using an automatic cell sorter. The automatic cell sorter may be one that is able to be used in a GMP process. For example, it may be a closed-system automatic cell sorter that is closed off from the external environment.

In the next step, 4-1BB expression is induced in the PBMCs isolated from cancer patient blood by culturing these PBMCs in a medium comprising a combination of the selected epitopes and cytokines.

Because cancer antigen-specific CD8+ T cells are present in the blood at a low concentration of 0.1% or less, by adding one or more cytokines and 3-4 peptides selected via epitope screening to PBMCs isolated from blood and then incubating for 7 to 9 days, it is possible to proliferate CD8+ T cells specific to peptides derived from cancer antigens and induce 4-1BB expression (FIG. 1.B-1, B-2). As a result, the total incubation time may be reduced to 29 days or less, 26 days or less, 20 days or less, 18 days or less, and in particular 15 days.

In one embodiment according to the present application, the cytokine may be any one selected from the group of IL-2, IL-7, IL-15 and IL-21. In another embodiment, the cytokine may be a combination of at least two selected from the group of IL-2, IL-7, IL-15, and IL-21. For example, the cytokine may be a combination of IL-2 and IL-7, IL-2 and IL-15, IL-2 and IL-21, IL-7 and IL-15, IL-7 and IL-21, or IL-15 and IL-21.

The proliferation of conventional cancer antigen-specific CD8+ T cells is carried out over 14 days of culture, and on day 14 of culture, additional reactivation for 24 hours is required in order to induce 4-1BB expression in antigen-specific CD8+ T cells.

In this embodiment, step b) of the present application may be performed over a period of 7, 8, 9, 10, 11, 12, 13 or 14 days.

In view of the purpose of the present application, the peripheral blood mononuclear cells (PBMCs) used in the first and second steps of the method according to the present application are from the same patient. PBMCs may be isolated from whole blood using methods known in the art.

In a third step, antigen-specific cells induced with 4-1BB expression are isolated after staining using anti-4-1BB antibody and anti-CD8 antibody. Isolation may be performed using, for example, an automatic cell sorter. The isolation of antigen-specific 4-1BB+CD8+ T cells using an automatic cell sorter may improve several problems caused by the conventional process using a plate coated with 4-1BB antibody, such as purity and difficulty of work. With the 4-1BB protein, after staining a marker that is expressed only on the surface of CD8+ T cells stimulated by the antigen and is coupled to a fluorescent labeling agent using an anti-CD8 antibody and a 4-1BB antibody, the antigen-specific CD8+ T cells that have both kinds of fluorescence may be isolated efficiently.

As described above, the preparation method in which CD8+ T cells expressing 4-1BB+ are selected using an automatic cell sorter may be used in the preparation of CD8+ T cells that are specific for cancer antigens such as EBV, hTERT, NY-ESO-1, WT1, and MAGE-A3. As described above, the pharmaceutical composition prepared by the method of selecting CD8+ T cells expressing 4-1BB+ using an automatic cell sorter may comprise at least 90% of cancer antigen-specific cytotoxic T cells (for example, 90%, 91%, 92%, 93%, 94%, 95%, 96%, 97%, 98%, or 99%).

A pharmaceutical composition (for example, a composition comprising cytotoxic T cells that are specific for BV, CMV, hTERT, NY-ESO-1, WT1, or MAGE-A3) prepared by a preparation method in which CD8+ T cells expressing 4-1BB+ are selected using an automatic cell sorter as described above has high purity of the cancer antigen-specific cytotoxic T cells, and thus has superior clinical efficacy as a T cell therapeutic (for example, anti-cancer efficacy and the like).

The automatic cell sorter used in the above screening step may be one that can be used in a GMP process. For example, it may be a closed-system automatic cell sorter.

The method according to the present application further comprises a step of mass propagating these isolated 4-1BB+ CD8+ T cells.

The mass propagation step may comprise a step of culturing the isolated cancer antigen-specific CD8+ T cells and irradiated allogeneic PBMCs in a medium comprising IL-2, anti-CD3 antibody and autologous plasma.

In one embodiment, 4-1BB+ CD8+ T cells ($5\times10^5$-$3\times10^6$ cells), irradiated allogeneic PBMCs ($1\times10^8$-$3\times10^8$ cells) isolated in a 1L culture vessel (culture bag or G-Rex device), 1000 U/mL IL-2, and 30 ng anti-CD3 mAb are mixed and added to medium at regular intervals over 7 to 11 days, and then the cells are mass-cultured so that they proliferate to a level greater than $1\times10^9$ cells/L at which they may be administered to a cancer patient.

The pharmaceutical composition for cancer prevention or treatment comprising the cancer antigen-specific cytotoxic T cell according to the present invention may comprise approximately $1\times10^6$ cells/mL or more, approximately $2\times10^6$ cells/mL or more, approximately $3\times10^6$ cells/mL or more, approximately $4\times10^6$ cells/mL or more, approximately $5\times10^6$ cells/mL or more, approximately $6\times10^6$ cells/mL or more, approximately $7\times10^6$ cells/mL or more, approximately $8\times10^6$ cells/mL or more, approximately $9\times10^6$ cells/mL or more, approximately $1\times10^7$ cells/mL or more, approximately $2\times10^7$ cells/mL or more, approximately $3\times10^7$ cells/mL or more, approximately $4\times10^7$ cells/mL or more, approximately $5\times10^7$ cells/mL or more, approximately $6\times10^7$ cells/mL or more, approximately $7\times10^7$ cells/mL or more, approximately $8\times10^7$ cells/mL or more, approximately $9\times10^7$ cells/mL or more, approximately $1\times10^8$ cells/mL or more, approximately $2\times10^8$ cells/mL or more, approximately $3\times10^8$ cells/mL or more, approximately $4\times10^8$ cells/mL or more, approximately $5\times10^8$ cells/mL or more, approximately $6\times10^8$ cells/mL or more, approximately $7\times10^8$ cells/mL or more, approximately $8\times10^8$ cells/mL or more, or approximately $9\times10^8$ cells/mL or more, but a person of ordinary skill in the art will be able to adjust the concentration of cytotoxic T cells within the range in which the same effects may be obtained. In addition, of the cells comprised in the pharmaceutical composition of the present invention, about 90% or more are CD8+ T cells.

The cancer antigen is at least one selected from the group of OY-TES-1, hTERT, NY-ESO1, MAGE-A3, WT1, PSMA, TARP, mesothelin, tyrosinase, GP100, MNRT-1, PAP, PSA, CMV, HCV, HBV, MC polyoma virus, HPV and EBV.

The "composition" disclosed in this invention refers to a combination of the cytotoxic T cells according to the present invention as the active ingredient, and inactive ingredients such as natural or artificial carriers, labels or detectors, an active ingredients such as adjuvants, diluents, coupling agents, stabilizers, buffers, salts, lipophilic solvents, and preservatives, and comprises a pharmaceutically acceptable carrier. The carrier may also comprise pharmaceutical excipients and additional proteins, peptides, amino acids, lipids, and carbohydrates (for example, monosaccharides; disaccharides; trisaccharides; tetrasaccharides; oligosaccharides; alditol, aldonic acid, sugar-derived polysaccharides such as esterified sugar, or a sugar polymer or the like), alone or in combination, at 1 to 99.99 wt % or vol %. Protein excipients include, for example, human serum albumin, recombinant human albumin, gelatin, casein, and the like, but are not limited thereto. Representative amino acid components that may play a buffer role include, for example, alanine, arginine, glycine, betaine, histidine, glutamic acid, aspartic acid, cysteine, lysine, leucine, isoleucine, valine, methionine, phenylalanine, aspartame, and the like, but are not limited thereto.

Carbohydrate excipients also include, for example, monosaccharides such as fructose, maltose, galactose, glucose, D-mannose, sorbose; disaccharides such as lactose, sucrose, trehalose, cellobiose; polysaccharides such as raffinose, maltodextrin, dextran, and starch; and alditols such as mannitol, xylitol, maltitol, lactitol, sorbitol, and myoinositol; but are not limited thereto.

A skilled person will be able to formulate the pharmaceutical composition of the present invention by methods known in the art. For example, as required, it may be used parenterally in the form of an injection of a sterile solution or suspension with water or another pharmaceutically acceptable liquid. For example, it may be appropriately combined with pharmaceutically acceptable carriers or media, in particular sterile water or saline solution, vegetable oil, emulsifier, suspension agent, surfactant, stabilizer, excipient, vehicle, preservative, binder and the like; it may be formulated by mixing in a unit-dosage form required by generally accepted pharmaceutical practice. The active ingredient amount used in the formulation is such that a suitable dosage in the indicated range may be obtained.

In addition, sterile compositions for injection may be formulated according to conventional formulation practice using excipient liquids, such as distilled water for injection. As the aqueous solution for injection may be used, for example, combinations of physiological saline; isotonic solutions comprising glucose or other auxiliary agents, for example D-sorbitol, D-mannose, D-mannitol, sodium chloride, and suitable dissolution aids, for example alcohols, in particular ethanol, and polyalcohols, for example propylene glycol, polyethylene glycol; and nonionic surfactants such as polysorbate 80™, HCO-50. Oily liquids include for example sesame oil and soybean oil, and may be used in combination with benzyl benzoate and benzyl alcohol as a dissolution aid.

Injection formulations may for example be administered by intravenous injection, intraarterial injection, selective intraarterial injection, intramuscular injection, intraperitoneal injection, subcutaneous injection, intraventricular injection, intracranial injection, intramedullary injection, and the like; preferably, however, they are administered by intravenous injection.

The composition of the present invention comprises a pharmaceutically effective amount of T cells. The effective amount may be readily determined by persons of ordinary skill in the art based on the disclosure in this specification. In general, a pharmaceutically effective amount is determined by 1st administering a low concentration of an active ingredient, and then gradually increasing the concentration until a desired effect is achieved in the subject without any side effects (for example, the symptoms associated with cancer are reduced or eliminated). Methods of determining appropriate dosages or intervals of administration for the administration of the compositions according to the present invention are described, for example, in Goodman and Gilman's The Pharmacological Basis of Therapeutics, Goodman et al., eds., 11th Edition, McGraw-Hill 2005, and Remington: The Science and Practice of Pharmacy, 20th and 21st Editions, Gennaro and University of the Sciences in Philadelphia, Eds., Lippencott Williams & Wilkins (2003 and 2005).

The method of administration of the composition according to the present invention may be determined based on various factors such as the subject's type of cancer, age, weight, sex, medical condition, severity of the disease, route of administration, and other medications to be administered separately. Accordingly, although the method of administration varies widely, it may be determined according to a commonly used method.

The amount of the composition according to the present invention to be administered to a subject may be determined by numerous factors such as the method of administration, subject's state of health, weight, and medical advice; all of these factors are within the scope of knowledge of a person of ordinary skill in the art.

The pharmaceutical composition for cancer prevention or treatment comprising the cancer antigen-specific cytotoxic T cell according to the present invention may comprise approximately $1 \times 10^6$ cells/mL or more, approximately $2 \times 10^6$ cells/mL or more, approximately $3 \times 10^6$ cells/mL or more, approximately $4 \times 10^6$ cells/mL or more, approximately $5 \times 10^6$ cells/mL or more, approximately $6 \times 10^6$ cells/mL or more, approximately $7 \times 10^6$ cells/mL or more, approximately $8 \times 10^6$ cells/mL or more, approximately $9 \times 10^6$ cells/mL or more, approximately $1 \times 10^7$ cells/mL or more, approximately $2 \times 10^7$ cells/mL or more, approximately $3 \times 10^7$ cells/mL or more, approximately $4 \times 10^7$ cells/mL or more, approximately $5 \times 10^7$ cells/mL or more, approximately $6 \times 10^7$ cells/mL or more, approximately $7 \times 10^7$ cells/mL or more, approximately $8 \times 10^7$ cells/mL or more, approximately $9 \times 10^7$ cells/mL or more, approximately $1 \times 10^8$ cells/mL or more, approximately $2 \times 10^8$ cells/mL or more, approximately $3 \times 10^8$ cells/mL or more, approximately $4 \times 10^8$ cells/mL or more, approximately $5 \times 10^8$ cells/mL or more, approximately $6 \times 10^8$ cells/mL or more, approximately $7 \times 10^8$ cells/mL or more, approximately $8 \times 10^8$ cells/mL or more, or approximately $9 \times 10^8$ cells/mL or more, but a person of ordinary skill in the art will be able to adjust the concentration of cytotoxic T cells within the range in which the same effects may be obtained.

It may also be combined with buffers, for example phosphate buffer solutions or sodium acetate buffer solutions; analgesics, for example procaine hydrochloride; stabilizers, for example benzyl alcohol, phenols and antioxidants. The prepared injection solution is usually charged into a suitable ampoule.

Suspensions and emulsions may comprise as carriers, for example, natural gums, agar, sodium alginate, pectin, methyl cellulose, carboxy methyl cellulose, or polyvinyl alcohol. Suspensions or solutions for intramuscular injection comprise, together with the active compound, pharmaceutically acceptable carriers such as sterile water, olive oil, ethyl oleate, glycols, for example, propylene glycol, and, if necessary, appropriate quantities of lidocaine hydrochloride.

Pharmaceutical compositions comprising cytotoxic T cells according to the present invention may be administered to a subject, for example, by venous injection (bolus injection) or continuous infusion. For example, the pharmaceutical composition according to the present invention may be administered at least 1 time, at least 2 times, at least 3 times, at least 4 times, or at least 5 times, continuously, or at specified time intervals, over 1 hour or less, at least 1 hour, at least 2 hours, at least 3 hours, at least 4 hours at least 8 hours, at least 12 hours, at least 1 day, at least 2 days, at least 3 days, at least 4 days, at least 5 days, at least 6 days, at least 7 days, at least 2 weeks, at least 3 weeks, at least 4 weeks, at least 1 month, at least 3 months, at least 6 months, or at intervals determined by clinical judgment. Injectable preparations may be formulated in ampoule form or in a unit dosage form with a multi-dose container. However, a person of ordinary skill in the art will understand that the dosage of the pharmaceutical composition according to the present invention may vary depending on various factors such as the subject's age, weight, height, sex, general medical condition and previous treatment history.

As used in the present invention, the term "cancer" refers to any of the numerous diseases or disorders caused by abnormal, uncontrolled cell growth. The cells that may cause cancer are called cancer cells, and have unique typological characteristics such as uncontrolled proliferation, immortality, metastatic potential, rapid growth and proliferation. Often, cancer cells may be in the form of a tumor, but such cells may be present individually in mammals or may be non-tumor cells, such as leukemia cells. Cancer may be detected by a clinical or radiological method for detecting the presence of tumors; by testing cells from tumors or other biological samples obtained by means such as biopsies; by detecting cancer blood markers such as CA125, PAP, PSA, CEA, AFP, HCG, CA19-9, CA15-3, CA27-29, LDH, and NSE; or by detecting cancer marker genotypes such as TP53 and ATM. However, a negative finding by an above method does not necessarily mean a non-cancer diagnosis: For example, a subject who has been found to have fully recovered from cancer may still have cancer, as relapses confirm.

As used in the present specification, the term "about" refers to a range commonly used in the art, for example, within 2 standard deviations of the mean. "About" may be understood to mean within 50%, 45%, 40%, 35%, 30%, 25%, 20%, 15%, 10%, 9%, 8%, 7%, 6%, 5%, 4%, 3%, 2%, 1%, 0.5%, 0.1%, 0.05%, or 0.01% of the mentioned value.

As used herein, the term "anti-cancer" encompasses "prevention" and "treatment"; "prevention" means any action in which cancer is inhibited or delayed by administration of a composition comprising the antibody of the present invention, and "treatment" means any action that improves or beneficially alters the symptoms of cancer by administering the antibody of the present invention.

Hereinbelow, the present invention is explained in detail with reference to the following embodiments. These embodiments are intended to more concretely illustrate the present invention, and they do not limit the invention's scope.

Practical Example 1: Cancer Antigen Selection and CD8+ T Cell Epitope Screening

EBV (Epstein-Bar virus) is the most common and widespread disease that infects in childhood and usually causes no symptoms, but immune memory is present in the majority of people. EBV is also a cause of various EBV-positive tumors. Accordingly, patient-specific epitope screening was performed as follows using EBV antigen as a representative antigen that can induce an immune response in both healthy individuals and cancer patients.

EBV amino acid sequences were analyzed with conventional algorithms (CTLPred: http://www.imtech.res.in/raghava/ctlpred/, NetCTL: http://www.cbs.dtu.dk/services/NetCTL/, SYFPEITHI: http://www.syfpeithi.de/) was used to determine the amino acid sequence presumed to be a CD8+ T cell epitope, and the selected epitope peptide was chemically synthesized (Peptron Inc; www.peptron.com) and used for epitope screening.

CD8+ T cell epitopes selected from EBV antigens are shown in Table 1 below.

TABLE 1

Amino Acid sequence of EBV LPM2a (Latent Membrane Protein 2a) CD8 T cell epitope

| | |
|---|---|
| EBV LMP2a-1 GLGTLGAAI (SEQ ID NO: 5) | EBV LMP2a-10 ILTAGFLIFL (SEQ ID NO: 14) |
| EBV LMP2a-2 LTAGFLIFL (SEQ ID NO: 6) | EBV LMP2a-11 TYGPVFMSL (SEQ ID NO: 15) |
| EBV LMP2a-3 LIVDAVLQL (SEQ ID NO: 7) | EBV LMP2a-12 TYGPVFMCL (SEQ ID NO: 16) |
| EBV LMP2a-4 CLGGLLTMV (SEQ ID NO: 8) | EBV LMP2a-13 PYLFWLAAI (SEQ ID NO: 17) |
| EBV LMP2a-5 FLYALALLI (SEQ ID NO: 9) | EBV LMP2a-14 IYVLVMLVL (SEQ ID NO: 18) |
| EBV LMP2a-6 TVCGGIMFL (SEQ ID NO: 10) | EBV LMP2a-15 AYRRRWRRL (SEQ ID NO: 19) |
| EBV LMP2a-7 LLWTLVVLL (SEQ ID NO: 11) | EBV LMP2a-16 RYCCYYCLTL (SEQ ID NO: 20) |
| EBV LMP2a-8 GLATLVAML (SEQ ID NO: 12) | EBV LMP2a-17 LYALALLLL (SEQ ID NO: 21) |
| EBV LMP2a-9 SLGGLLTMV (SEQ ID NO: 13) | EBV LMP2a-18 SYAAAQRKLL (SEQ ID NO: 22) |

Screening of epitopes with high T-cell reactivity was performed over the steps described in FIG. 1 (A: total 15 days with conventional epitope screening method; B: total 7 days with epitope screening method according to the present application), using the EBV CD8+ T cell epitopes selected in Table 1.

Specifically, EBV CD8+ T cell epitope screening was performed using peripheral blood mononuclear cells (PBMCs) of an EBV-positive healthy individual donor. After isolating the PBMCs from the peripheral blood and washing them, they were suspended in CTL (Cytotoxic T Lymphocyte) medium (RPMI1640 medium+4 mM L-glutamine+12.5 mM HEPES+50 µM 2-mercaptoethanol+3% autologous plasma) at $1 \times 10^6$ cells/mL and 1 mL each was aliquoted into 14 mL round tubes. The selected epitope peptides were then respectively added to a respective tube at a concentration of 2 µg/mL and cultured in a $CO_2$ incubator.

Then, in the process according to the present application, on the second day of culture, 1 mL of CTL medium comprising 100 U/mL IL-2 was added to each tube. Culture broth was collected from each tube on day 7 of culture and the amount of IFN-γ was analyzed using a cytometric bead array (BD Bioscience) according to the manufacturer's method.

In the case of the conventional epitope screening method, 1 mL of medium was removed on days 7, 9, 11, and 13 days of culture, and 1 mL of CTL medium comprising 100 U/mL IL-2 was then added. On day 14 of culture, RPMI1640 medium was added to each tube, and the cells were washed 3 times by centrifugation at 1400 rpm for 5 minutes. After suspending the washed cells in 1 mL CTL medium, the same epitope peptide was added at 2 µg/mL and incubated.

After 24 hours, cells from each tube were harvested, stained with anti-CD8-PE-Cy5 and anti-4-1BB-PE antibody (BD Bioscience) for flow cytometry, and the proportion of CD8+ T expressing 4-1BB was analyzed in order to analyze the epitope peptides that activated the CD8+ T cells.

In the conventional epitope screening method, the antigen epitopes that strongly induced the expression of 4-1BB in CD8+ T cells were found to be those numbered 1, 3, 9, 11, 13, and 14 (FIG. 2A). In the case of the epitope screening method according to the present application, the quantity of IFN-γ from the culture medium on day 7 indicated strong production of the epitope peptides 1, 9, 11, 13 in the culture broth (FIG. 2B).

The results indicate that cancer antigen epitopes selected through IFN-γ production in the epitope screening method according to the present application, and cancer antigen epitopes selected through 4-1BB expression analysis in conventional CD8+ T cells, were similar. These results indicate that the method according to the present application is capable of screening the cancer antigen epitopes necessary for the production of T cell therapeutics in a short time of no more than 7 days, while also making the process simpler compared to the conventional method and reducing the time by upwards of 50% from 15 days to 7 days. The conventional method selects up to 4 antigen epitopes that increase 4-1BB-expressing CD8+ T cells in a 15-day process; the method of the present application selects up to 4 antigen epitopes based on IFN-γ production in a 7-day process. The two methods selected similar antigen epitopes, but above all, the process according to the present application not only addressed the problems of the 15-day screening in the conventional process, but also is more accurate, because it measures the IFN-γ produced by the antigen-specific CD8+ T cells that are currently proliferating. Practical examples of T cell proliferation using selected epitopes are presented in FIGS. 5 and 6.

Practical Example 2: Pilot Production of Antigen-Specific Cell Therapeutic According to the Method of the Present Application (20-Day Process)

The majority of people are infected with CMV (cytomegalovirus) during the growth process, forming immune memory of T cells, having strong antigenicity so as to induce proliferation of antigen-specific CD8+ T cells; MEW class I pentamers for detecting antigen-specific CD8+ T cells have also been developed and are commercially available. Accordingly, the test production of the antigen-specific CD8+ T cell therapeutic was performed according to the steps described in FIG. 3 using blood of a CMV positive healthy individual. Production of T cell therapeutics consists of the three steps of proliferation, isolation, and mass culture of CD8+ T cells that are specific for epitope peptides; the specific experimental methods and results are as follows.

2-1. Proliferation of Antigen-Specific CD8+ T Cells

PBMCs were isolated from blood of a CMV-positive healthy individual as follows. 7 mL of blood was slowly flowed into a 15 mL conical tube filled with 7 mL Ficoll-hypaque and overlaid on top of the Ficoll solution. The tube was centrifuged at room temperature at 2000 rpm for 20 minutes, and only the white cell layer located between the Ficoll and the plasma was collected, washed, and used for PBMC.

Autoplasma was then isolated from the light yellow layer above the PBMC layer, filtered using a filter, and then used.

The isolated PBMCs were then suspended in CTL medium (RPMI1640 medium+4 mM L-glutamine+12.5 mM HEPES+50 μM 2-mercaptoethanol+3% autoplasma) at $1\times10^6$ cells/mL, and CMV peptide was added at 2 μL/mL (NLVPMVATV (SEQ ID NO: 23), CMV/pp65 495-504, Peptron Ltd.) to reach a concentration of 2 μg/mL. These cell suspensions were then aliquoted at 1 mL each into 14 mL round tubes and incubation was begun in a $CO_2$ incubator.

On the second day of culture, 1 mL of CTL medium comprising 100 U/mL IL-2 (Proleukin, Novatis)+3% autoplasma was added to each tube.

After 7 days of culture, 1 mL supernatant medium was removed, and CTL medium comprising 100 U/mL IL-2+3% autoplasma was added and incubated for another 2 days.

2-2. Selective Isolation of Antigen-Specific CD8+ T Cells

On day 9 of culture, PBMCs in culture were collected and washed twice with PBS (phosphate buffered saline). The washed PBMCs were stained with anti-4-1BB antibody and anti-CD8 antibody at 4° C. for 30 minutes and then washed twice with PBS. After staining, the washed PBMCs were isolated using an automatic cell sorter (manufacturer and model name 1: Miltenyi bio tec, Tyto; manufacturer and model name 2: BD Bioscience, BD FACSAria) and washed twice with RPMI1640 medium. Subsequently, cells were counted with an automatic cell counter (EVE Automatic cell counter, NanoEnTek), and suspended at $5\times10^5$ cells/mL using ALyS505N medium (CELL SCIENCE & TECHNOLOGY INST., INC.), and then the next step was conducted.

2-3. Mass Culture of Antigen-Specific CD8+ T Cells

PBMCs were isolated from 200 mL of healthy donor blood, suspended at $1\times10^7$ cells/mL, then irradiated at 3000 rad to induce cell death, and then a culture additive that could provide the co-stimulation necessary to induce proliferation of T cells was added.

Into a 50 mL conical tube was added $5\times10^5$ antigen-specific CD8+ T cells isolated in Practical Example 2-1 and $1\times10^8$ irradiated allogeneic PBMCs, followed by up to 50 ml of ALyS505N medium comprising 1,000 U/mL IL-2, 30 ng/mL anti-CD3 mAb (BD Bioscience) and 3% autoplasma. The 50 mL cell suspension was injected into a 1L culture vessel (1L culture bag (NIPRO) or 1L G-Rex device (Wilson Wolf)), and then incubated in a $CO_2$ incubator.

On day 3 of culture, 150 mL of ALyS505N medium comprising 1,000 U/mL IL-2, 3% autologous plasma was additionally injected into the 1L culture vessel. On day 6 of culture, 300 mL of ALyS505N medium comprising 1,000 U/mL IL-2, 3% autologous plasma was additionally injected into the 1L culture vessel. On day 9 of culture, 500 mL of ALyS505N medium comprising 1,000 U/mL IL-2, 3% autologous plasma was additionally injected into a 1L culture vessel. On day 11 of culture, all cells from the 1L culture vessel were collected, washed three times with physiological saline injection solution, and suspended in physiological saline injection solution comprising 5% albumin to charge the finished T cell therapeutic.

As a result, the antigen-specific CD8+ T cells produced in the 20-day process were found to be CMV specific CD8+ T cells (FIG. 3) with CD3+, CD8+, CD45RO+, CD45RA−, CD62L− (CD62L+; ~7.4%), CCR7−, and CD27− (CD27+; ~7.5%) phenotypes.

The finished product was analyzed in accordance with the currently-effective evaluation criteria for finished T cell therapeutics (Ministry of Food and Drug Safety, self-evaluation criteria for clinical trials of finished T cell therapeutics).

Test items of the evaluation criteria are as described in Table 2, namely: 1) Total cell count test: Test of whether the produced T cells were produced in conformity with the finished product evaluation criteria. 2) Cell viability: Test of whether the viability of the produced T cell therapeutic is above the evaluation criterion level of 70%. 3) Confirmation test: Test of whether the finished product has a CD8+ T cell ratio of at least 65%. CD45RA is tested for whether the produced T cells have a Naive CD8+ T phenotype, and CD45RO is tested for whether the produced T cells have an Effector/Memory CD8+ T phenotype. 4) Purity test: Residue test to determine, for CD57, for how many senescent CD8+ T cells are present; for PD-1, for how many non-functional CD8+ T cells (exhausted CD8+ T) are present; for anti-CD3, how much of the antibodies used in mass production are left over in the finished product. 5) Cell function test: TCRvβ typing tests whether CD8+ T cells with particular TCR types for the antigen-epitopes that were introduced for cell production were produced at a level of at least 20%; IFN-γ production and LAMP1 expression tests how many CD8+ T cells have antigen-specific action mechanisms.

Practical Example 3: Pilot Production of EBV-Specific CD8+ T Cell Therapeutics According to the Method of the Present Application (20-Day Process)

3-1. Proliferation of EBV-Specific CD8+ T Cells

PBMC was isolated from the blood of an EBV-positive healthy individual, and in the process of item 2-1 of Example 2, EBV peptide was used instead of CMV peptide, and the EBV peptide that was used was selected through the process of Practical Example 1.

TABLE 2

| Test item | | Test criterion | Conventional production process (using plate coated with anti-4-1BB antibody) | New production process (using automatic cell sorter) |
|---|---|---|---|---|
| Total cell count test | | $7.0 \times 10^6$ cell/mL + 10% 100 mL/infusion bag | $6.7 \times 10^6$ cell/ml, 200 mL, 2 bags | $6.9 \times 10^6$ cell/mL, 200 mL, 2 bags |
| Cell viability test | | >70% | ~92.3% | ~95.0% |
| Verification test | CD8 T | >65% | 65.0% to 85.0% | ~95.0% |
| | CD45RA | 20% of CD8 T cells | ~13.3% | ~1.7% |
| | CD45RO | >80% of CD8 T cells | ~98.5% | ~99.7% |
| Purity test | CD57 | 35% of CD8 T cells | ~19.5% | ~16.8% |
| | PD-1 | 20% of CD8 T cells | ~2.3% | ~2.1% |
| | anti-CD3 mAb | Negative | Negative | Negative |
| Cell function test | IFN-γ production | >10% of CD8 T cells | ~54.4% | ~43% |
| | LAMP1 Expression | >10% of CD8 T cells | ~83.2% | ~65% |
| Quality testing | Sterility test | Negative | — | — |
| | Endotoxin test | <1.0 EU/mL | — | — |
| | Mycoplasma test | Negative | — | — |
| | External virus suitability test | Negative | — | — |

Figure 4D:
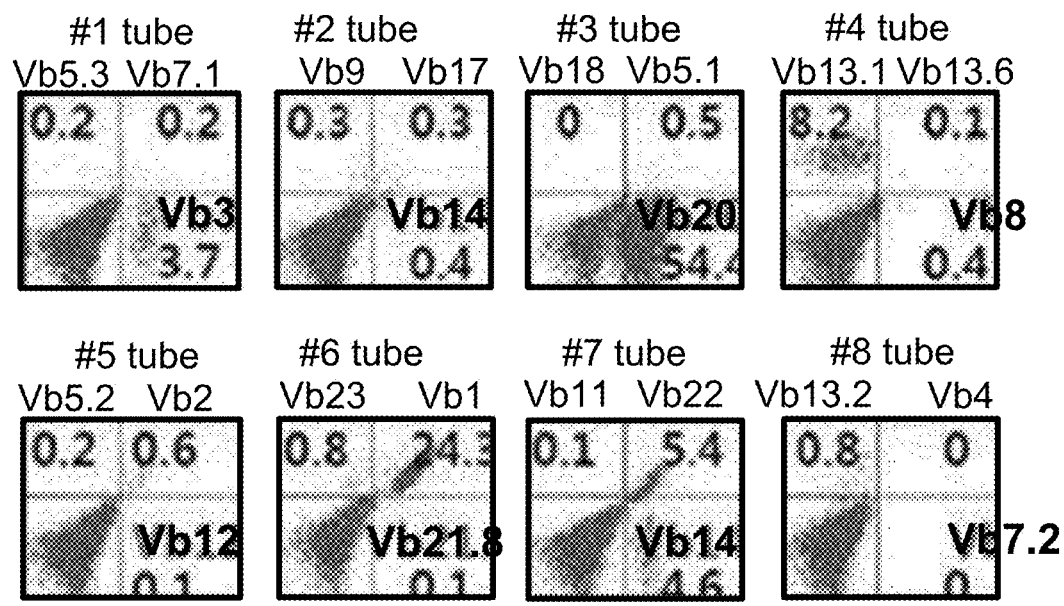
Figure 4E:
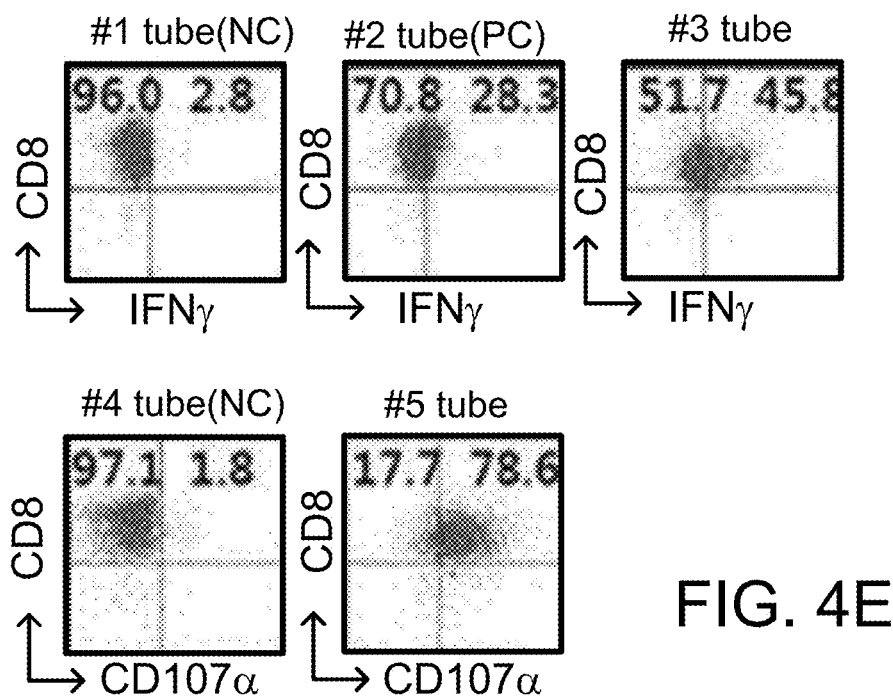

The analysis confirmed that the T cell therapeutic had been produced in conformity with the T cell therapeutic self-evaluation criteria and test items approved by the Food and Drug Administration (FIG. 4).

In addition, comparison of the quality of the T cell therapeutics produced according to the conventional production process (cell isolation process using the plate coated with anti-4-1BB antibody) and the cell isolation process using an automatic cell sorter according to the present application as described above, in accordance with the test items and test criteria presented in Table 2, showed that although the T cell therapeutics produced in both processes were suitable for conducting a clinical trial (FIG. 4), the total cell count, purity, and viability of the T cell therapeutics produced according to the method of the present application were superior.

In particular, the majority of CD8+ T cell therapeutics produced by the process according to the present application were found to have a purity of at least 95%. These results indicate that the method according to the present application is able to straightforwardly and quickly produce high-purity T cells in a shorter time than the conventional method.

3-2. Selective Isolation of EBV-Specific CD8+ T Cells

Procedure 2-2 of Practical Example 2 was performed in the same manner, but using FACSMelody of BD Bioscience for the automatic cell sorter, and LUNA-FL of Logos Biosystems for the automatic cell counter.

3-3. Mass Culture of Antigen-Specific CD8+ T Cells

Healthy donor blood was irradiated to induce cell death, and PBMCs were isolated and then suspended at $1 \times 10^7$ cells/mL and frozen. Irradiated PBMCs (allogenic PBMCs) were used as a culture additive to provide the co-stimulation necessary to induce the proliferation of T cells. The isolated alloplasma was then isolated from the light yellow layer on the upper layer of PBMC, filtered using a filter, and then used.

In a 50 mL tube, selectively isolated CD8+ T cells specific for EBV peptide and irradiated allogenic PBMCs, prepared at 200 times the isolated cell count, were suspended in 30 mL of ALys505N medium comprising 3% alloplasma. To this were added 1,000 IU/mL IL-2 and 30 ng/mL anti-CD3 antibody. 30 mL of the cell suspension was then placed in a 75T flask and incubation was begun in a $CO_2$ incubator.

On day 3 of culture, 20 mL of ALys505N medium comprising 1,000 IU/mL IL-2, 3% alloplasma was added to the 75T flask. On days 5 to 15 of culture, at 2-3 day intervals, the same quantity of ALys505N medium comprising 1,000 IU/mL IL-2, 3% alloplasma was added. On day 15 of culture, all cultured cells were harvested.

As described above, the confirmation and purity test results for the EBV-specific CD8+ T cells produced from 5 donors in the 20-day process, shown in Table 2 below, confirmed that all the criteria shown in Table 2 were satisfied.

TABLE 3

| Donor | CD8 (%) (>80%) | CD57: CD8 (%) (<35%) | PD-1: CD8 (%) (<20%) | CD45RA: CD8 (%) (<20%) | CD45RO: CD8 (%) (>80%) |
|---|---|---|---|---|---|
| 1 | 95.58 | 7.02 | 3.82 | 0.63 | 97.86 |
| 2 | 91.19 | 12.70 | 2.27 | 12.81 | 85.36 |
| 3 | 96.65 | 11.21 | 5.36 | 3.45 | 86.00 |
| 4 | 96.17 | 6.40 | 6.30 | 1.16 | 88.46 |
| 5 | 94.72 | 27.25 | 2.68 | 1.94 | 97.79 |

In addition, the results of the potency test, as shown in the table below, all satisfied the evaluation criteria of Table 2.

TABLE 4

| Donor | LAMP-1: CD8 (%) (>10%) | IFN-g: CD8 (%) (>10%) |
|---|---|---|
| 1 | 29.5 | 48.4 |
| 2 | 13.53 | 12.88 |
| 3 | 15.15 | 18.75 |
| 4 | 30.20 | 48.02 |
| 5 | 35.06 | 19.94 |

Practical Example 4: Pilot Production of EBV Specific CD8+ T Cell Therapeutic According to the Method of the Present Application (26-Day Process)

4-1. Proliferation of EBV-Specific CD8+ T Cells

Process 3-1 of Practical Example 3 was carried out identically.

4-2. Selective Isolation of EBV-Specific CD8+ T Cells

On day 14 of culture, PBMCs in culture were harvested and washed in RPMI medium. The washed PBMCs were counted with an automatic cell counter (Logos Biosystems, LUNA-FL), and the cells were suspended in CTL medium so that the cells could be cultured at $2\times10^6$ cells/mL. 3% autoplasma and 100 IU/mL IL-2 were added to the CTL medium in which the cells were suspended, and then the cells suspended at $2\times10^6$ cells per 1 mL were placed in each well of a 24-well plate. hTERT, WT1, NY-ESO-1 peptides added on the first day of culture were added to reach a concentration of 2 μg/mL and incubated in a $CO_2$ incubator.

On day 15 of culture, PBMCs in culture were harvested and washed in RPMI medium. The washed PBMCs were stained with anti-4-1BB antibody and anti-CD8 antibody at 4° C. for 30 minutes, and then washed again with RPMI medium.

After staining, the washed PBMCs were selectively isolated from cells expressing 4-1BB and CD8 using an automatic cell sorter (BD Biosciences, FACSMelody). Selectively isolated cells were washed with RPMI medium and the cells were counted with an automatic cell counter. The isolated cells were suspended using ALyS505N medium and then the next step was performed.

Figure 7:
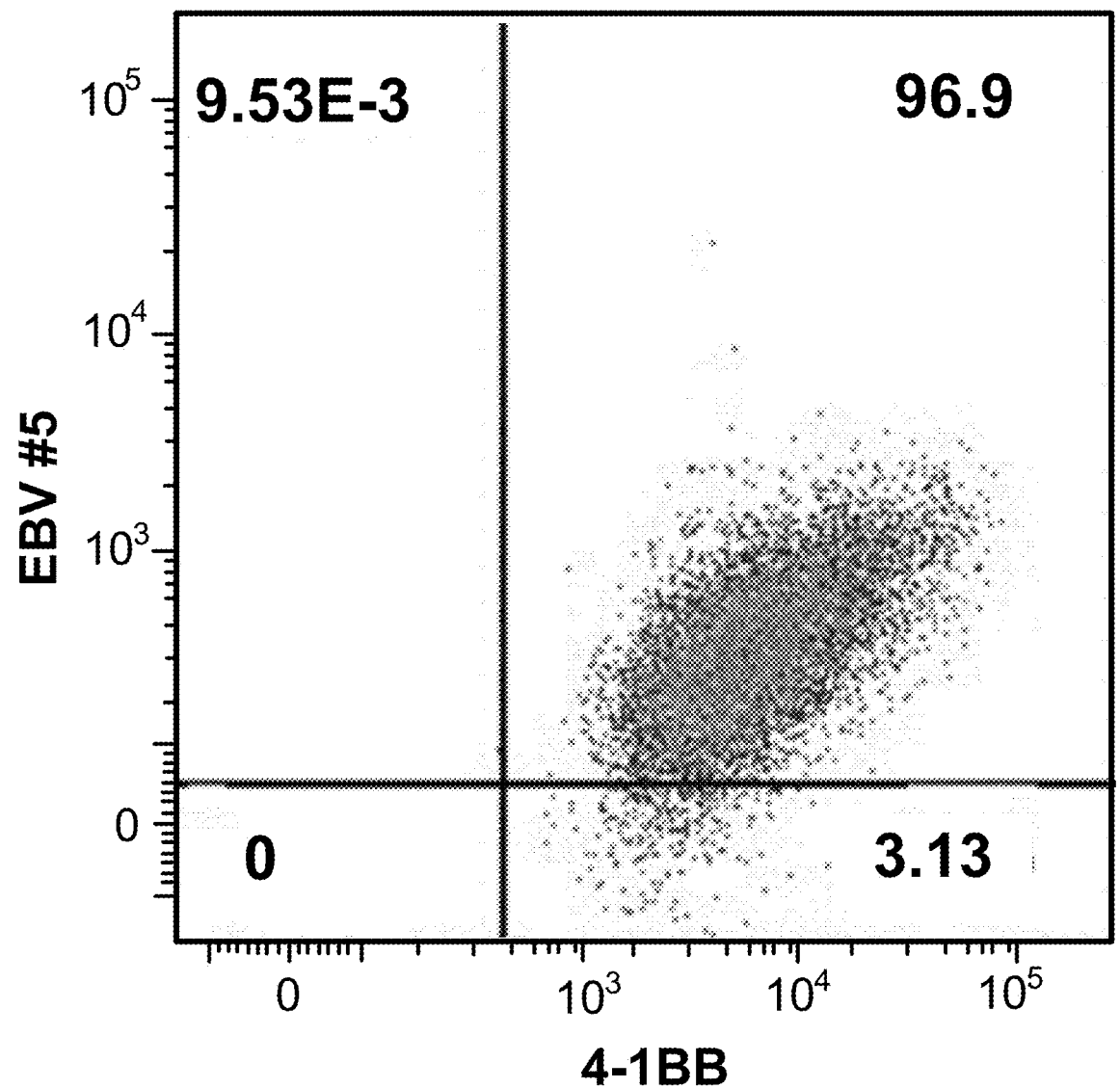
FIGS. 7 and 8 show the results of isolating EBV-specific CD8+ T cells using an automatic cell sorter and analyzing them using a flow cytometer.
Figure 8:
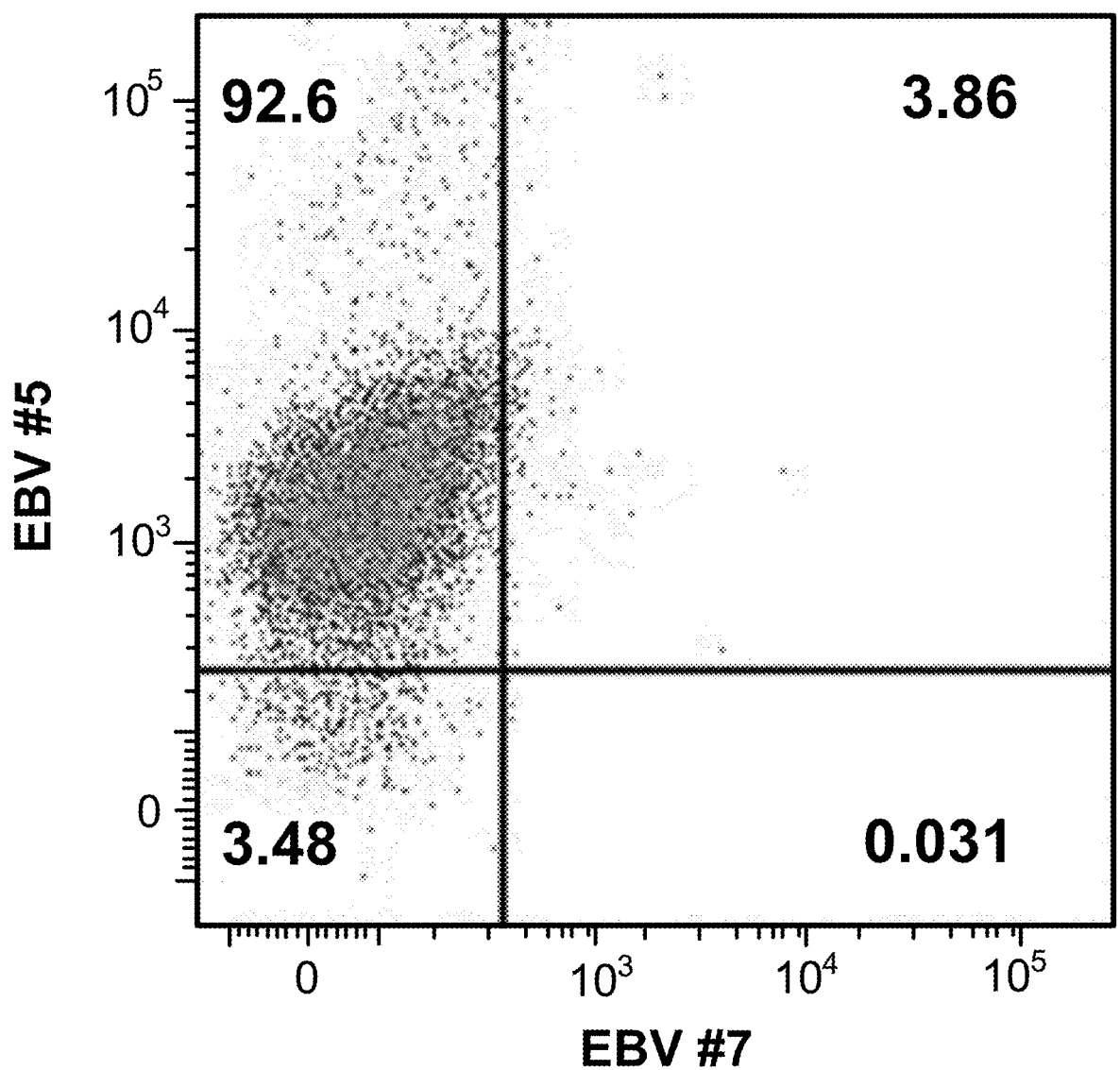

In the case of Donor 5, process 4-1 of Practical Example 4 was carried out identically, using the peptide corresponding to EBV5; The CD8+4-1BB+ cells isolated via an automatic cell sorter were stained using PE-MHC Class I Pentamer (Proimmune, A*02: 01 FLYALALLL (SEQ ID NO: 24) and analyzed using a flow cytometer (BD Biosciences, FACSCelesta). As a result, it was confirmed that 96.9% of the cells were EBV-specific CD8+ T cells. (FIG. 7 and FIG. 8)

4-3. Mass Culture of Antigen-Specific CD8+ T Cells

Healthy donor blood was irradiated to induce cell death, PBMCs were isolated and suspended at $1\times10^7$ cells/mL and then frozen and stored. Irradiated PBMCs (allogenic PBMCs) were used as a culture additive to provide the co-stimulation necessary to induce the proliferation of T cells. The isolated alloplasma was then isolated from the light yellow layer on the upper layer of PBMC, filtered using a filter, and then used.

In a 50 mL tube, selectively isolated CD8+ T cells specific for EBV peptide and irradiated allogenic PBMCs, prepared at 200 times the isolated cell count, were suspended in 30 mL of ALys505N medium comprising 3% alloplasma. To this was added 1,000 IU/mL IL-2 and 30 ng/mL anti-CD3 antibody. 30 mL of the cell suspension was then placed in a 75T flask and incubation was begun in a $CO_2$ incubator.

On day 3 of culture, 20 mL of ALys505N medium comprising 1,000 IU/mL IL-2, 3% alloplasma was added to the 75T flask. On days 5 to 11 of culture, at 2-3 day intervals, the same quantity of ALys505N medium comprising 1,000 IU/mL IL-2, 3% alloplasma was added. On day 11 of culture, all cultured cells were harvested.

As described above, the confirmation and purity test results for the antigen-specific CD8+ T cells produced in the 26-day process, shown in Table 5 below, confirmed that all the criteria shown in Table 2 were satisfied.

TABLE 5

| Donor | CD8 (%) (>80%) | CD57: CD8 (%) (<35%) | PD-1: CD8 (%) (<20%) | CD45RA: CD8 (%) (<20%) | CD45RO: CD8 (%) (>80%) |
|---|---|---|---|---|---|
| 5 | 97.47 | 4.60 | 6.97 | 1.03 | 98.49 |
| 6 | 99.13 | 8.31 | 2.27 | 6.28 | 90.25 |

In addition, the potency test result confirmed that the potency test criteria of Table 2 were satisfied, as shown in Table 6 below.

TABLE 6

| Donor | LAMP-1 (%) (>10%) | IFN-g (%) (>10%) |
|---|---|---|
| 5 | 22.28 | 24.19 |
| 6 | 10.07 | 17.10 |

Practical Example 5: Pilot Production of EBV-Specific CD8+ T Cell Therapeutics According to the Method of the Present Application (29-Day Process)

5-1. Proliferation of EBV-Specific CD8+ T Cells

Process 4-1 of Practical Example 4 was carried out identically.

5-2. Selective Isolation of EBV-Specific CD8+ T Cells

Process 4-2 of Practical Example 4 was carried out identically.

5-3. Mass Culture of EBV-Specific CD8+ T Cells

Process 4-3 of Example 4 was performed in the same manner, but with the difference that at 2-3 day intervals, until day 14 rather than day 11 of culture, ALys505N medium comprising 1,000 IU/mL IL-2 and 3% alloplasma was added in the same quantity, and on day 14 of culture, all the cultured cells were collected.

As described above, the confirmation and purity test results for the antigen-specific CD8+ T cells produced in the 29-day process, shown in Table 7 below, confirmed that all the criteria shown in Table 2 were satisfied.

TABLE 7

| Donor | CD8 (%) (>80%) | CD57: CD8 (%) (<35%) | PD-1: CD8 (%) (<20%) | CD45RA: CD8 (%) (<20%) | CD45RO: CD8 (%) (>80%) |
|---|---|---|---|---|---|
| 7 | 98.6 | 1.85 | 2.92 | 1.25 | 97.94 |

In addition, the potency test result confirmed that the potency test criteria of Table 2 were satisfied, as shown in Table 8 below.

TABLE 8

| Donor | LAMP-1 (%) (>10%) | IFN-g (%) (>10%) |
|---|---|---|
| 7 | 21.50 | 44.81 |

To confirm the antigenic specificity of cells produced by mass culture, cell surface staining was carried out on the cells of donor 7 produced with EBV peptide 5, using PE-MHC Class I Pentamer (Proimmune, A*02: 01 FLY-ALALLL (SEQ ID NO: 25) and APC-MHC Class I Pentamer (Proimmune, A*02: 01 LLWTLVVLL (SEQ ID NO: 26), and it was confirmed that 92.6% were EBV #5-specific CD8+ T cells. (FIG. 8)

Practical Example 6: Pilot Production of Antigen-Specific CD8+ T Cell Therapeutic According to the Method of the Present Application (15-Day Process)

The differences from the 20-day process of Practical Example 3 are as follows. In the 20-day process, incubation for primary proliferation was conducted in the presence of IL-2, but in the 15-day process, CD8+ T cells were proliferated in the presence of a combination of cytokines, i.e. for example, IL-2+IL-21. In the case of mass culture, in the 20-day process, $5 \times 10^5$ antigen-specific CD8+ T cells and $1 \times 10^8$ irradiated allogeneic PBMCs were used, but in the 15-day process, $1.5 \times 10^6$ CD8+ T cells and $3 \times 10^8$ allogeneic PBMCs were used. In addition, the total culture broth is the same at 1 L, but the quantity of culture broth added during the process is different.

Figure 5:
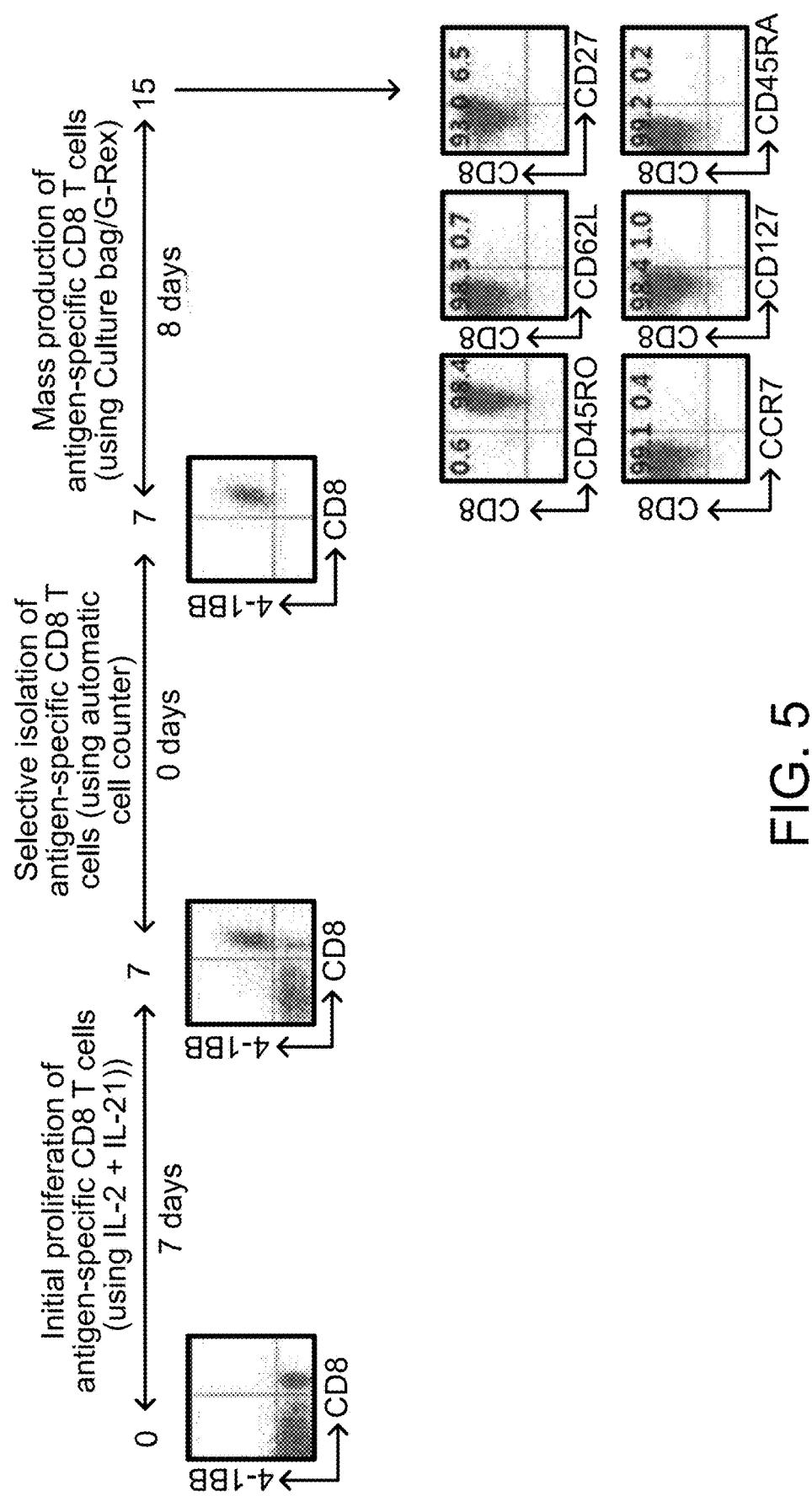
FIG. 5 shows the results of confirmation of the phenotype of the antigen-specific CD8+ T cells produced by the antigen-specific CD8+ T cell therapeutic production process and the 15-day process.
Figure 6A:
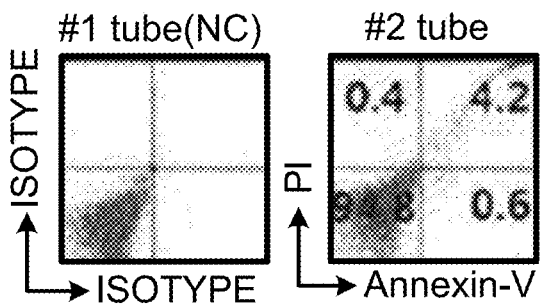
FIGS. 6A-6E show the results of testing against the self-assessment criteria and the test items for the T cell therapeutic product.
Figure 6B:
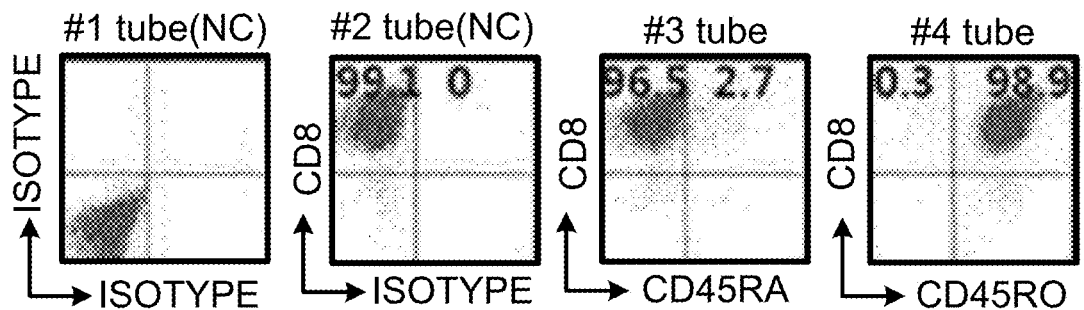
Figure 6C:
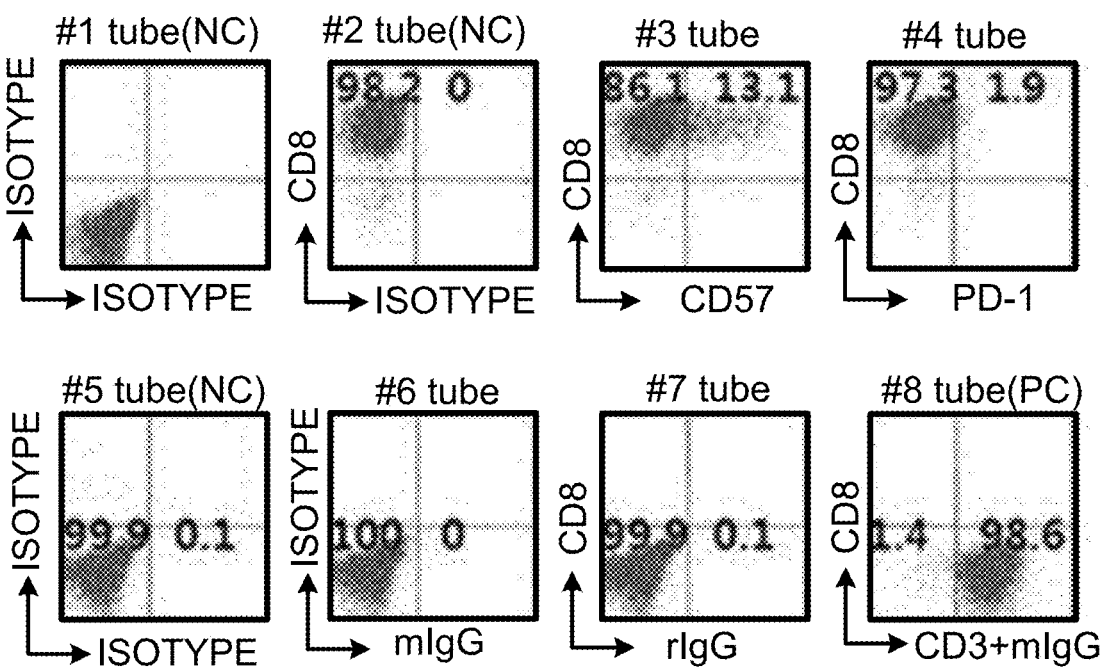
Figure 6D:
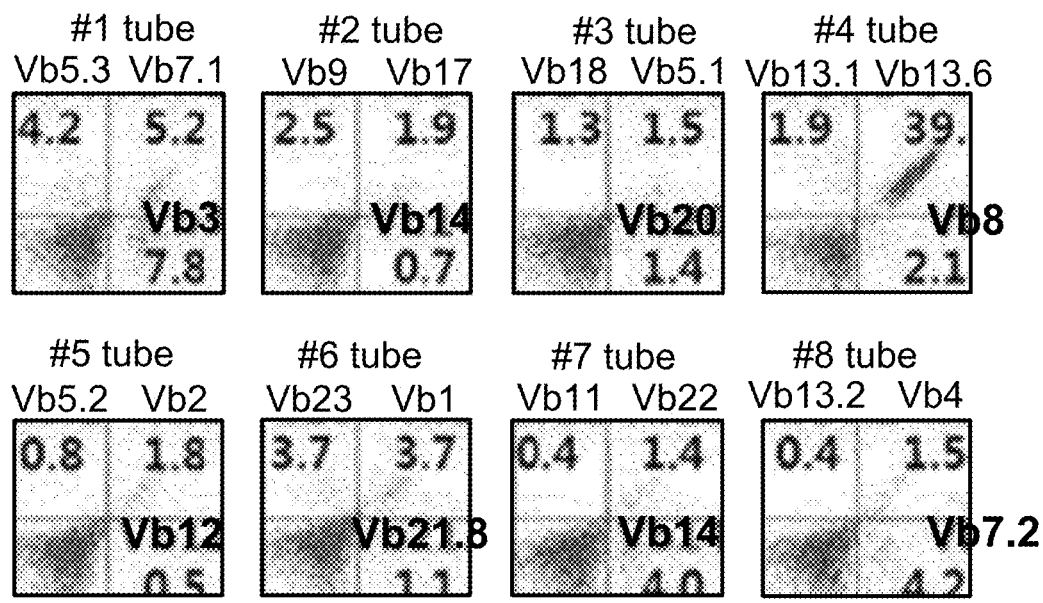
Figure 6E:
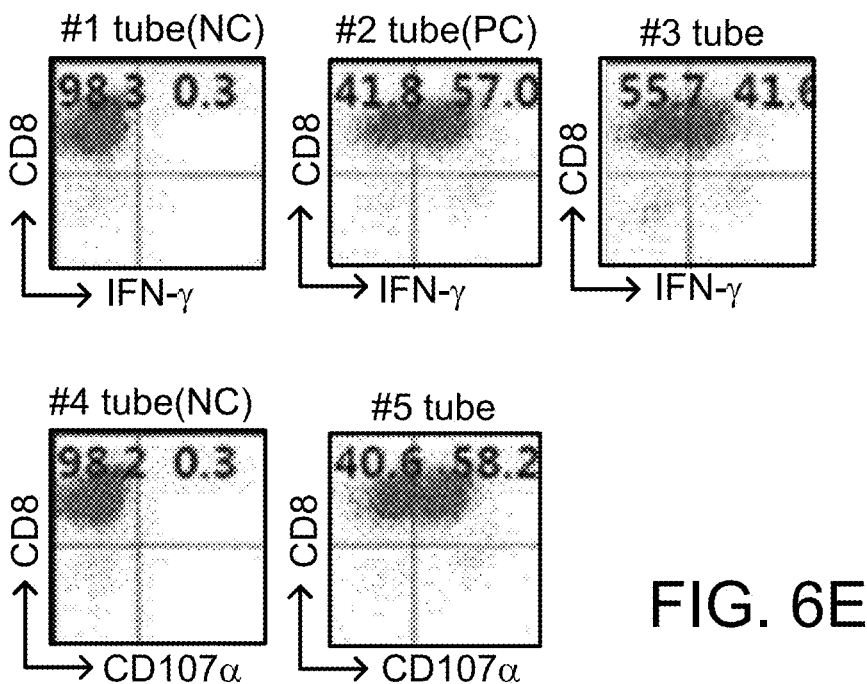

Accordingly, the test production of the antigen-specific T cell therapeutic was performed according to the steps described in FIG. 5 using blood of an EBV-positive healthy individual. The specific experimental methods and results are as follows.

6-1. Proliferation of Antigen-Specific CD8+ T Cells

PBMCs were isolated from the blood of an EBV-positive healthy individual as follows. 7 mL of blood was slowly flowed into a 15 mL conical tube filled with 7 mL Ficoll-hypaque and overlaid on top of the Ficoll solution. The tube was centrifuged at room temperature at 2000 rpm for 20 minutes, and only the white cell layer located between the Ficoll and the plasma was collected, washed, and used for PBMC. Autoplasma was then isolated from the light yellow layer above the PBMC layer, filtered using a filter, and then used.

Next, the isolated PBMCs were suspended at $1 \times 10^6$ cells/mL in CTL medium (RPMI1640 medium+4 mM L-glutamine+12.5 mM HEPES+50 µM 2-mercaptoethanol+3% autoplasma), and EBV peptides (EBV LMP2a-I GLGTLGAAI (SEQ ID NO: 27), EBV LMP2a-9 SLG-GLLTMV (SEQ ID NO: 28), EBV LMP2a-11 TYGPVFMSL (SEQ ID NO: 29), EBV LMP2a-13 PYLFW-LAAI (SEQ ID NO: 30), Keppetron) were respectively added to reach 2 µg/mL concentration. These cell suspensions were then aliquoted at 1 mL each into 14 mL round tubes and incubation was begun in a $CO_2$ incubator.

On the second day of culture, 1 mL of CTL medium containing 100 U/mL IL-2 (Proleukin, Novatis)+10 U/mL IL-21 (Miltenyi Bio tec)+3% autoplasma was added to each tube and incubated for an additional 5 days.

6-2. Selective Isolation of Antigen-Specific CD8+ T Cells

On day 7 of culture, PBMCs in culture were collected and washed twice with PBS (phosphate-buffered saline). The washed PBMCs were stained with anti-4-1BB antibody and anti-CD8 antibody at 4° C. for 30 minutes and then washed twice with PBS. After staining, the washed PBMCs were isolated using an automatic cell sorter (Miltenyi bio tec, Tyto; manufacturer and model name 2: BD Bioscience, BD FACSAria) and washed twice with RPMI1640 medium.

Cells were counted with an automatic cell counter (EVE Automatic cell counter, NanoEnTek), and suspended at $5 \times 10^5$ cells/mL using ALyS505N medium (CELL SCIENCE & TECHNOLOGY INST., INC. (CSTI)).

6-3. Mass Culture of Antigen-Specific CD8+ T Cells

PBMCs were isolated from 300 mL of healthy donor blood, suspended at $1 \times 10^7$ cells/mL, then irradiated at 3000 rad to induce cell death, and then a culture additive that could provide the co-stimulation necessary to induce proliferation of T cells was added.

$1.5 \times 10^6$ isolated antigen-specific CD8+ T cells and $3 \times 10^8$ irradiated allogeneic PBMCs, 1,000 U/mL IL-2, 30 ng/mL anti-CD3 mAb (BD Bioscience) and 3% autoplasma were added to 200 mL of ALyS505N medium. The 200 mL cell suspension was injected into a 1 L culture vessel (1L culture bag (NIPRO) or 1L G-Rex device (Wilson Wolf)), and then incubated in a $CO_2$ incubator.

On day 3 of culture, 300 mL of ALyS505N medium comprising 1,000 U/mL IL-2, 3% autologous plasma was additionally injected into the 1L culture vessel. On day 6 of culture, 500 mL of ALyS505N medium comprising 1,000 U/mL IL-2, 3% autologous plasma was additionally injected into the 1L culture vessel, and incubated for an additional 2 days. On day 8 of culture, all cells from the 1L culture vessel were collected, washed three times with physiological saline injection solution, and suspended in physiological saline injection solution comprising 5% albumin to charge the finished T cell therapeutic.

The quality of the T cell therapeutic was then examined.

As a result, the antigen-specific CD8+ T cells produced in the 15-day process as described in FIG. 5 were high-purity antigen specific CD8+ T cells with CD3+, CD8+, CD45RO+, CD45RA, CD62L−, CCR7−, and CD27− (CD27+~6.5%) phenotypes. As shown in Table 2, when the finished product was analyzed according to the cell therapeutic finished-product evaluation criteria, it was confirmed that the T cell therapeutic product suitable for the evaluation criteria was produced as shown in FIG. 6.

Practical Example 7: Toxicity Test Result of Finished Drug of EBV-Derived Antigen-Specific CD8+ T Cell (EBViNT Cell)

The repeated-dose toxicity test results of the mouse-derived CTL treatment group and placebo group were as follows. 1) No dead animals or general symptoms were observed during the experimental period. 2) No changes were observed in body weight, feed and water intake, and result of eye examination, urinalysis and hematological examination. 3) As a result of blood biochemical test and organ weight measurement, no change due to test substance was observed. 4) There was no change due to test substance in the autopsy and histopathologic findings.

Accordingly, the repeated intravenous administration of mouse-derived CTL on 4 occasions over 3 weeks in female and male mice of the C57BL/6N line did not induce any toxicological effect in death rate, general symptoms, weight change, feed and water intake, eye examination, urinalysis, hematological and serum chemistry examinations, autopsy findings, organ weight, and histopathological examination. Accordingly, under these test conditions, the non-toxic amount of the test substance (NOAEL: no observed adverse effect level) was found to be $6 \times 10^6$ cells/head in both male and female animals, and no target organs were observed.

Practical Example 8: Distribution Test Results of Drugs of EBViNT Cell Finished Product After administering EBViNT Cell finished product, the distribution was verified in vivo.

Day 10 of CD8 T cell administration was the most potent time for the CD8 T cell response to be administered; when 0.7-fold CD8+ T cells were administered, a low proportion (less than 0.1-0.2%) was detected only in the secondary lymphoid organs of some mice (male #3, female #8). When 7-fold CD8+ T cells were administered, the administered CD8+ T cells were detected at around 1-5% in the majority of secondary lymphoid organs (inguinal, axillary, cervical, mesenteric LN and spleen). Among other organs, the administered CD8+ T cells were detected at 0.5-7% only in the lungs; the administered CD8+ T cells were not detected in the kidney, bone marrow, brain, liver, thymus, heart, and testis/ovary sex organs.

Day 30 of CD8+ T cell administration is the time when the administered CD8+ T cell response forms immune memory, and CD8+ T cells exhibiting active function decrease, and only some memory T cells responsible for immune memory remain. When $3.32 \times 10^5$ CD8+ T cells were administered, in all mice, no CD8+ T cells were detected. When $3.32 \times 10^6$ CD8+ T cells were administered, only the CD8+ T cells administered in secondary lymphoid organs (inguinal, axillary, cervical, mesenteric LN and spleen) of male #1-5 live mice were detected at around 2%; in other organs such as the kidney, bone marrow, brain, liver, lung, thymus, heart and testis/ovary sex organs, the administered CD8+ T cells were not detected.

Accordingly, it was determined that the majority of antigen-specific CD8+ T cells migrate to secondary lymphoid organs, accumulate and proliferate, and that cancer antigen-specific CD8+ T cells administered to ordinary organs did not exhibit accumulation or proliferation.

For example, for claim construction purposes, it is not intended that the claims set forth below be construed in any way narrower than the literal language thereof, and it is thus not intended that exemplary embodiments from the specification be read into the claims. Accordingly, it is to be understood that the present invention has been described by way of illustration and not by way of limiting the scope of the claims. Accordingly, the present invention is limited only by the following claims. All publications, issued patents, patent applications, books and journal articles, cited in the present application are each incorporated into this application by reference in their entirety.

The invention claimed is:

1. A method of treating cancer with a pharmaceutical composition, wherein the pharmaceutical composition is manufactured by a method comprising:
   (a) selecting one or more cancer antigen-derived epitopes of a cancer antigen of hTERT, NY-ESO1, MAGE-A3, WT1, or EBV;
   (b) incubating one or more peripheral blood mononuclear cell (PBMC) populations isolated from the blood of the subject having cancer with a cancer antigen-derived epitope from the one or more cancer antigen-derived epitopes of the cancer antigen, and at least one cytokine selected from the group consisting of IL-2, IL-7, IL-15, and IL-21;
   (c) isolating T cells expressing both CD8 and 4-1BB from the one or more PBMC populations produced in step (b);
   (d) incubating the isolated T cells selected in step (c) with anti-CD3 antibody and IL-2; and
   (e) administering to the cancer patient a therapeutically effective amount of the pharmaceutical composition, wherein the pharmaceutical composition comprises at least about $7 \times 10^6$ cells/mL of cancer antigen-specific cytotoxic T cells, and wherein at least about 90% of the at least about $7 \times 10^6$ cells/mL are CD8+ T cells, and either at least 80% of the CD8+ T cells are CD45RO-expressing cells, or 20% or less of the CD8+ T cells are CD45RA-expressing cells.

2. The method according to claim 1, wherein step (a) comprises selecting two or more cancer antigen-derived epitopes of a cancer antigen of hTERT, NY-ESO1, MAGE-A3, WT1, or EBV.

3. The method according to claim 1, wherein step (c) is performed using a closed-system flow cytometer.

4. The method of claim 1, selecting one or more PBMC population(s) from step (b) which have IFN-γ in an amount of more than 50 pg/ml of culture medium as the cells to be isolated in step (c) using an IFN-gamma screen comprising measuring IFN-gamma production using a cytometric bead array.

5. A method of manufacturing a pharmaceutical composition for treating cancer in a subject having cancer, comprising:
   (a) selecting one or more cancer antigen-derived epitopes of a cancer antigen of hTERT, NY-ESO1, MAGE-A3, WT1, or EBV;
   (b) incubating one or more peripheral blood mononuclear cell (PBMC) populations isolated from the blood of the subject having cancer with a cancer antigen-derived epitope from the one or more cancer antigen-derived epitopes of the cancer antigen, and at least one cytokine selected from the group consisting of IL-2, IL-7, IL-15, and IL-21;
   (c) isolating T cells expressing both CD8 and 4-1BB from the one or more PBMC populations produced in step (b); and
   (d) incubating the isolated T cells selected in step (c) with anti-CD3 antibody and IL-2; and wherein the pharmaceutical composition comprises at least about $7 \times 10^6$ cells/mL of cancer antigen-specific cytotoxic T cells, and wherein at least about 90% of the at least about $7 \times 10^6$ cells/mL are CD8+ T cells, and either at least 80% of the CD8+ T cells are CD45RO-expressing cells, or 20% or less of the CD8+ T cells are CD45RA-expressing cells.

6. The method according to claim 5, wherein step (a) comprises selecting two or more cancer antigen-derived epitopes of a cancer antigen of hTERT, NY-ESO1, MAGE-A3, WT1, or EBV.

7. The method according to claim 5, wherein step (c) is performed using a closed-system flow cytometer.

8. The method of claim 5, selecting one or more PBMC population(s) from step (b) which have IFN-γ in an amount of more than 50 pg/ml of culture medium as the cells to be isolated in step (c) using an IFN-gamma screen comprising measuring IFN-gamma production using a cytometric bead array.

9. The method of claim 5, further comprising freezing a the pharmaceutical composition obtained in (d).

10. A pharmaceutical composition of at least about $7 \times 10^6$ cells/mL for treating cancer in a subject having cancer, wherein the pharmaceutical composition is manufactured by a method comprising:
- (a) selecting one or more cancer antigen-derived epitopes of a cancer antigen of hTERT, NY-ESO1, MAGE-A3, WT1, or EBV;
- (b) incubating one or more peripheral blood mononuclear cell (PBMC) populations isolated from the blood of the subject having cancer with a cancer antigen-derived epitope from the one or more cancer antigen-derived epitopes of the cancer antigen and at least one cytokine selected from the group consisting of IL-2, IL-7, IL-15, and IL-21;
- (c) isolating T cells expressing both CD8 and 4-1BB from the one or more PBMC populations produced in step (b); and
- (d) incubating the isolated T cells selected in step (c) with anti-CD3 antibody and IL-2, such that at least about 90% of the at least about $7 \times 10^6$ cells/mL are CD8+ T cells, and either at least 80% of the CD8+ T cells are CD45RO-expressing cells, or 20% or less of the CD8+ T cells are CD45RA-expressing cells.

11. The pharmaceutical composition for treating cancer according to claim 10, wherein step (a) comprises selecting two or more cancer antigen-derived epitopes of a cancer antigen of hTERT, NY-ESO1, MAGE-A3, WT1, or EBV.

12. The pharmaceutical composition for treating cancer according to claim 10, wherein step (c) is performed using a closed-system flow cytometer.

13. The pharmaceutical composition of claim 10, selecting one or more PBMC population(s) from step (b) which have IFN-γ in an amount of more than 50 pg/ml of culture medium as the cells to be isolated in step (c) using an IFN-gamma screen comprising measuring IFN-gamma production using a cytometric bead array.

14. The pharmaceutical composition of claim 10, wherein the method further comprises freezing a the pharmaceutical composition obtained in (d).

* * * * *

SEQUENCE LISTING

```
<160> NUMBER OF SEQ ID NOS: 30

<210> SEQ ID NO 1
<211> LENGTH: 1069
<212> TYPE: PRT
<213> ORGANISM: Homo sapiens

<400> SEQUENCE: 1

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110
```

```
Glu Ala Phe Thr Thr Ser Val Arg Ser Tyr Leu Pro Asn Thr Val Thr
            115                 120                 125

Asp Ala Leu Arg Gly Ser Gly Ala Trp Gly Leu Leu Leu Arg Arg Val
        130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro His Ala Ser Gly
                180                 185                 190

Pro Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
        260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
                340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
                420                 425                 430

Gly Ser Val Ala Ala Pro Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
                500                 505                 510

Ser Val Arg Asp Cys Ala Trp Leu Arg Arg Ser Pro Gly Val Gly Cys
        515                 520                 525
```

-continued

```
Val Pro Ala Ala Glu His Arg Leu Arg Glu Ile Leu Ala Lys Phe
530                 535                 540

Leu His Trp Leu Met Ser Val Tyr Val Glu Leu Leu Arg Ser Phe
545                 550                 555                 560

Phe Tyr Val Thr Glu Thr Thr Phe Gln Lys Asn Arg Leu Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
            595                 600                 605

His Arg Glu Ala Arg Pro Ala Leu Leu Thr Ser Arg Leu Arg Phe Ile
610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
                660                 665                 670

Pro Gly Leu Leu Gly Ala Ser Val Leu Gly Leu Asp Asp Ile His Arg
                675                 680                 685

Ala Trp Arg Thr Phe Val Leu Arg Val Arg Ala Gln Asp Pro Pro
690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
                740                 745                 750

Gly His Val Arg Lys Ala Phe Lys Ser His Val Ser Thr Leu Thr Asp
                755                 760                 765

Leu Gln Pro Tyr Met Arg Gln Phe Val Ala His Leu Gln Glu Thr Ser
770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
                820                 825                 830

Gln Gly Ser Ile Leu Ser Thr Leu Leu Cys Ser Leu Cys Tyr Gly Asp
                835                 840                 845

Met Glu Asn Lys Leu Phe Ala Gly Ile Arg Arg Asp Gly Leu Leu Leu
850                 855                 860

Arg Leu Val Asp Asp Phe Leu Leu Val Thr Pro His Leu Thr His Ala
865                 870                 875                 880

Lys Thr Phe Leu Ser Tyr Ala Arg Thr Ser Ile Arg Ala Ser Leu Thr
                885                 890                 895

Phe Asn Arg Gly Phe Lys Ala Gly Arg Asn Met Arg Arg Lys Leu Phe
                900                 905                 910

Gly Val Leu Arg Leu Lys Cys His Ser Leu Phe Leu Asp Leu Gln Val
                915                 920                 925

Asn Ser Leu Gln Thr Val Cys Thr Asn Ile Tyr Lys Ile Leu Leu Leu
930                 935                 940

Gln Ala Tyr Arg Phe His Ala Cys Val Leu Gln Leu Pro Phe His Gln
```

```
                945                 950                 955                 960
Gln Val Trp Lys Asn Pro Thr Phe Phe Leu Arg Val Ile Ser Asp Thr
                    965                 970                 975
Ala Ser Leu Cys Tyr Ser Ile Leu Lys Ala Lys Asn Ala Gly Met Ser
                    980                 985                 990
Leu Gly Ala Lys Gly Ala Ala Gly Pro Leu Pro Ser Glu Ala Val Gln
                    995                 1000                1005
Trp Leu Cys His Gln Ala Phe Leu Leu Lys Leu Thr Arg His Arg
    1010                1015                1020
Val Thr Tyr Val Pro Leu Leu Gly Ser Leu Arg Thr Ala Gln Thr
    1025                1030                1035
Gln Leu Ser Arg Lys Leu Pro Gly Thr Thr Leu Thr Ala Leu Glu
    1040                1045                1050
Ala Ala Ala Asn Pro Ala Leu Pro Ser Asp Phe Lys Thr Ile Leu
    1055                1060                1065
Asp

<210> SEQ ID NO 2
<211> LENGTH: 449
<212> TYPE: PRT
<213> ORGANISM: Homo sapiens

<400> SEQUENCE: 2

Met Gly Ser Asp Val Arg Asp Leu Asn Ala Leu Leu Pro Ala Val Pro
1               5                   10                  15
Ser Leu Gly Gly Gly Gly Gly Cys Ala Leu Pro Val Ser Gly Ala Ala
                20                  25                  30
Gln Trp Ala Pro Val Leu Asp Phe Ala Pro Pro Gly Ala Ser Ala Tyr
            35                  40                  45
Gly Ser Leu Gly Gly Pro Ala Pro Pro Ala Pro Pro Pro Pro
        50                  55                  60
Pro Pro Pro Pro His Ser Phe Ile Lys Gln Glu Pro Ser Trp Gly Gly
65                  70                  75                  80
Ala Glu Pro His Glu Glu Gln Cys Leu Ser Ala Phe Thr Val His Phe
                85                  90                  95
Ser Gly Gln Phe Thr Gly Thr Ala Gly Ala Cys Arg Tyr Gly Pro Phe
                100                 105                 110
Gly Pro Pro Pro Pro Ser Gln Ala Ser Ser Gly Gln Ala Arg Met Phe
                115                 120                 125
Pro Asn Ala Pro Tyr Leu Pro Ser Cys Leu Glu Ser Gln Pro Ala Ile
            130                 135                 140
Arg Asn Gln Gly Tyr Ser Thr Val Thr Phe Asp Gly Thr Pro Ser Tyr
145                 150                 155                 160
Gly His Thr Pro Ser His His Ala Ala Gln Phe Pro Asn His Ser Phe
                165                 170                 175
Lys His Glu Asp Pro Met Gly Gln Gln Gly Ser Leu Gly Glu Gln Gln
                180                 185                 190
Tyr Ser Val Pro Pro Pro Val Tyr Gly Cys His Thr Pro Thr Asp Ser
            195                 200                 205
Cys Thr Gly Ser Gln Ala Leu Leu Leu Arg Thr Pro Tyr Ser Ser Asp
        210                 215                 220
Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
```

```
                        245                 250                 255
Ser Val Lys Trp Thr Glu Gly Gln Ser Asn His Ser Thr Gly Tyr Glu
            260                 265                 270

Ser Asp Asn His Thr Thr Pro Ile Leu Cys Gly Ala Gln Tyr Arg Ile
            275                 280                 285

His Thr His Gly Val Phe Arg Gly Ile Gln Asp Val Arg Arg Val Pro
            290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
            325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
            355                 360                 365

Gln Leu Lys Arg His Gln Arg Arg His Thr Gly Val Lys Pro Phe Gln
            370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
            405                 410                 415

Arg Trp Pro Ser Cys Gln Lys Lys Phe Ala Arg Ser Asp Glu Leu Val
            420                 425                 430

Arg His His Asn Met His Gln Arg Asn Met Thr Lys Leu Gln Leu Ala
            435                 440                 445

Leu

<210> SEQ ID NO 3
<211> LENGTH: 180
<212> TYPE: PRT
<213> ORGANISM: Homo sapiens

<400> SEQUENCE: 3

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
            35                  40                  45

Gly Ala Ala Arg Ala Ser Gly Pro Gly Gly Ala Pro Arg Gly Pro
50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
            85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
            115                 120                 125

Ser Gly Asn Ile Leu Thr Ile Arg Leu Thr Ala Ala Asp His Arg Gln
            130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
```

```
                       165                 170                 175

Gly Gln Arg Arg
            180

<210> SEQ ID NO 4
<211> LENGTH: 314
<212> TYPE: PRT
<213> ORGANISM: Homo sapiens

<400> SEQUENCE: 4

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Glu Ala Ala Ser Ser Ser Thr Leu Val Glu Val
        35                  40                  45

Thr Leu Gly Glu Val Pro Ala Ala Glu Ser Pro Asp Pro Pro Gln Ser
    50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser
                85                  90                  95

Thr Phe Pro Asp Leu Glu Ser Glu Phe Gln Ala Ala Leu Ser Arg Lys
            100                 105                 110

Val Ala Glu Leu Val His Phe Leu Leu Leu Lys Tyr Arg Ala Arg Glu
        115                 120                 125

Pro Val Thr Lys Ala Glu Met Leu Gly Ser Val Val Gly Asn Trp Gln
    130                 135                 140

Tyr Phe Phe Pro Val Ile Phe Ser Lys Ala Ser Ser Ser Leu Gln Leu
145                 150                 155                 160

Val Phe Gly Ile Glu Leu Met Glu Val Asp Pro Ile Gly His Leu Tyr
                165                 170                 175

Ile Phe Ala Thr Cys Leu Gly Leu Ser Tyr Asp Gly Leu Leu Gly Asp
            180                 185                 190

Asn Gln Ile Met Pro Lys Ala Gly Leu Leu Ile Ile Val Leu Ala Ile
        195                 200                 205

Ile Ala Arg Glu Gly Asp Cys Ala Pro Glu Glu Lys Ile Trp Glu Glu
    210                 215                 220

Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
        275                 280                 285

His Met Val Lys Ile Ser Gly Gly Pro His Ile Ser Tyr Pro Pro Leu
    290                 295                 300

His Glu Trp Val Leu Arg Glu Gly Glu Glu
305                 310

<210> SEQ ID NO 5
<211> LENGTH: 9
<212> TYPE: PRT
<213> ORGANISM: Artificial
<220> FEATURE:
```

```
<223> OTHER INFORMATION: EBV LPM2a (Latent Membrane Protein 2a) CD8 T
      cell epitope

<400> SEQUENCE: 5

Gly Leu Gly Thr Leu Gly Ala Ala Ile
1               5

<210> SEQ ID NO 6
<211> LENGTH: 9
<212> TYPE: PRT
<213> ORGANISM: Artificial
<220> FEATURE:
<223> OTHER INFORMATION: EBV LPM2a (Latent Membrane Protein 2a) CD8 T
      cell epitope

<400> SEQUENCE: 6

Leu Thr Ala Gly Phe Leu Ile Phe Leu
1               5

<210> SEQ ID NO 7
<211> LENGTH: 9
<212> TYPE: PRT
<213> ORGANISM: Artificial
<220> FEATURE:
<223> OTHER INFORMATION: EBV LPM2a (Latent Membrane Protein 2a) CD8 T
      cell epitope

<400> SEQUENCE: 7

Leu Ile Val Asp Ala Val Leu Gln Leu
1               5

<210> SEQ ID NO 8
<211> LENGTH: 9
<212> TYPE: PRT
<213> ORGANISM: Artificial
<220> FEATURE:
<223> OTHER INFORMATION: EBV LPM2a (Latent Membrane Protein 2a) CD8 T
      cell epitope

<400> SEQUENCE: 8

Cys Leu Gly Gly Leu Leu Thr Met Val
1               5

<210> SEQ ID NO 9
<211> LENGTH: 9
<212> TYPE: PRT
<213> ORGANISM: Artificial
<220> FEATURE:
<223> OTHER INFORMATION: EBV LPM2a (Latent Membrane Protein 2a) CD8 T
      cell epitope

<400> SEQUENCE: 9

Phe Leu Tyr Ala Leu Ala Leu Leu Ile
1               5

<210> SEQ ID NO 10
<211> LENGTH: 9
<212> TYPE: PRT
<213> ORGANISM: Artificial
<220> FEATURE:
<223> OTHER INFORMATION: EBV LPM2a (Latent Membrane Protein 2a) CD8 T
      cell epitope

<400> SEQUENCE: 10

Thr Val Cys Gly Gly Ile Met Phe Leu
1               5
```

```
<210> SEQ ID NO 11
<211> LENGTH: 9
<212> TYPE: PRT
<213> ORGANISM: Artificial
<220> FEATURE:
<223> OTHER INFORMATION: EBV LPM2a (Latent Membrane Protein 2a) CD8 T
      cell epitope

<400> SEQUENCE: 11

Leu Leu Trp Thr Leu Val Val Leu Leu
1               5

<210> SEQ ID NO 12
<211> LENGTH: 9
<212> TYPE: PRT
<213> ORGANISM: Artificial
<220> FEATURE:
<223> OTHER INFORMATION: EBV LPM2a (Latent Membrane Protein 2a) CD8 T
      cell epitope

<400> SEQUENCE: 12

Gly Leu Ala Thr Leu Val Ala Met Leu
1               5

<210> SEQ ID NO 13
<211> LENGTH: 9
<212> TYPE: PRT
<213> ORGANISM: Artificial
<220> FEATURE:
<223> OTHER INFORMATION: EBV LPM2a (Latent Membrane Protein 2a) CD8 T
      cell epitope

<400> SEQUENCE: 13

Ser Leu Gly Gly Leu Leu Thr Met Val
1               5

<210> SEQ ID NO 14
<211> LENGTH: 10
<212> TYPE: PRT
<213> ORGANISM: Artificial
<220> FEATURE:
<223> OTHER INFORMATION: EBV LPM2a (Latent Membrane Protein 2a) CD8 T
      cell epitope

<400> SEQUENCE: 14

Ile Leu Thr Ala Gly Phe Leu Ile Phe Leu
1               5                   10

<210> SEQ ID NO 15
<211> LENGTH: 9
<212> TYPE: PRT
<213> ORGANISM: Artificial
<220> FEATURE:
<223> OTHER INFORMATION: EBV LPM2a (Latent Membrane Protein 2a) CD8 T
      cell epitope

<400> SEQUENCE: 15

Thr Tyr Gly Pro Val Phe Met Ser Leu
1               5

<210> SEQ ID NO 16
<211> LENGTH: 9
<212> TYPE: PRT
<213> ORGANISM: Artificial
<220> FEATURE:
<223> OTHER INFORMATION: EBV LPM2a (Latent Membrane Protein 2a) CD8 T
      cell epitope

<400> SEQUENCE: 16
```

```
Thr Tyr Gly Pro Val Phe Met Cys Leu
1               5

<210> SEQ ID NO 17
<211> LENGTH: 9
<212> TYPE: PRT
<213> ORGANISM: Artificial
<220> FEATURE:
<223> OTHER INFORMATION: EBV LPM2a (Latent Membrane Protein 2a) CD8 T
      cell epitope

<400> SEQUENCE: 17

Pro Tyr Leu Phe Trp Leu Ala Ala Ile
1               5

<210> SEQ ID NO 18
<211> LENGTH: 9
<212> TYPE: PRT
<213> ORGANISM: Artificial
<220> FEATURE:
<223> OTHER INFORMATION: EBV LPM2a (Latent Membrane Protein 2a) CD8 T
      cell epitope

<400> SEQUENCE: 18

Ile Tyr Val Leu Val Met Leu Val Leu
1               5

<210> SEQ ID NO 19
<211> LENGTH: 9
<212> TYPE: PRT
<213> ORGANISM: Artificial
<220> FEATURE:
<223> OTHER INFORMATION: EBV LPM2a (Latent Membrane Protein 2a) CD8 T
      cell epitope

<400> SEQUENCE: 19

Ala Tyr Arg Arg Arg Trp Arg Arg Leu
1               5

<210> SEQ ID NO 20
<211> LENGTH: 10
<212> TYPE: PRT
<213> ORGANISM: Artificial
<220> FEATURE:
<223> OTHER INFORMATION: EBV LPM2a (Latent Membrane Protein 2a) CD8 T
      cell epitope

<400> SEQUENCE: 20

Arg Tyr Cys Cys Tyr Tyr Cys Leu Thr Leu
1               5                   10

<210> SEQ ID NO 21
<211> LENGTH: 9
<212> TYPE: PRT
<213> ORGANISM: Artificial
<220> FEATURE:
<223> OTHER INFORMATION: EBV LPM2a (Latent Membrane Protein 2a) CD8 T
      cell epitope

<400> SEQUENCE: 21

Leu Tyr Ala Leu Ala Leu Leu Leu Leu
1               5

<210> SEQ ID NO 22
<211> LENGTH: 10
<212> TYPE: PRT
<213> ORGANISM: Artificial
```

```
<220> FEATURE:
<223> OTHER INFORMATION: EBV LPM2a (Latent Membrane Protein 2a) CD8 T
      cell epitope

<400> SEQUENCE: 22

Ser Tyr Ala Ala Ala Gln Arg Lys Leu Leu
1               5                   10

<210> SEQ ID NO 23
<211> LENGTH: 9
<212> TYPE: PRT
<213> ORGANISM: Artificial
<220> FEATURE:
<223> OTHER INFORMATION: Synthetic peptide

<400> SEQUENCE: 23

Asn Leu Val Pro Met Val Ala Thr Val
1               5

<210> SEQ ID NO 24
<211> LENGTH: 9
<212> TYPE: PRT
<213> ORGANISM: Artificial
<220> FEATURE:
<223> OTHER INFORMATION: Synthetic peptide

<400> SEQUENCE: 24

Phe Leu Tyr Ala Leu Ala Leu Leu Leu
1               5

<210> SEQ ID NO 25
<211> LENGTH: 9
<212> TYPE: PRT
<213> ORGANISM: Artificial
<220> FEATURE:
<223> OTHER INFORMATION: Synthetic peptide

<400> SEQUENCE: 25

Phe Leu Tyr Ala Leu Ala Leu Leu Leu
1               5

<210> SEQ ID NO 26
<211> LENGTH: 9
<212> TYPE: PRT
<213> ORGANISM: Artificial
<220> FEATURE:
<223> OTHER INFORMATION: Synthetic peptide

<400> SEQUENCE: 26

Leu Leu Trp Thr Leu Val Val Leu Leu
1               5

<210> SEQ ID NO 27
<211> LENGTH: 9
<212> TYPE: PRT
<213> ORGANISM: Artificial
<220> FEATURE:
<223> OTHER INFORMATION: Synthetic peptide

<400> SEQUENCE: 27

Gly Leu Gly Thr Leu Gly Ala Ala Ile
1               5

<210> SEQ ID NO 28
<211> LENGTH: 9
<212> TYPE: PRT
<213> ORGANISM: Artificial
```

```
<220> FEATURE:
<223> OTHER INFORMATION: Synthetic peptide

<400> SEQUENCE: 28

Ser Leu Gly Gly Leu Leu Thr Met Val
1               5

<210> SEQ ID NO 29
<211> LENGTH: 9
<212> TYPE: PRT
<213> ORGANISM: Artificial
<220> FEATURE:
<223> OTHER INFORMATION: Synthetic peptide

<400> SEQUENCE: 29

Thr Tyr Gly Pro Val Phe Met Ser Leu
1               5

<210> SEQ ID NO 30
<211> LENGTH: 9
<212> TYPE: PRT
<213> ORGANISM: Artificial
<220> FEATURE:
<223> OTHER INFORMATION: Synthetic peptide

<400> SEQUENCE: 30

Pro Tyr Leu Phe Trp Leu Ala Ala Ile
1               5
```